(12) United States Patent
Lee, Jr. et al.

(10) Patent No.: US 9,382,267 B2
(45) Date of Patent: Jul. 5, 2016

(54) SMALL MOLECULE INHIBITORS OF NICOTINAMIDE PHOSPHORIBOSYLTRANSFERASE (NAMPT)

(71) Applicant: The Curators of the University of Missouri, Columbia, MO (US)

(72) Inventors: Mark Wayne Lee, Jr., Columbia, MO (US); Yulia Sevryugina, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 51 days.

(21) Appl. No.: 14/361,857

(22) PCT Filed: Nov. 28, 2012

(86) PCT No.: PCT/US2012/066849
§ 371 (c)(1),
(2) Date: May 30, 2014

(87) PCT Pub. No.: WO2013/082150
PCT Pub. Date: Jun. 6, 2013

(65) Prior Publication Data
US 2015/0322093 A1 Nov. 12, 2015

Related U.S. Application Data

(60) Provisional application No. 61/629,877, filed on Nov. 30, 2011.

(51) Int. Cl.
*C07F 5/05* (2006.01)
*C07D 213/56* (2006.01)
*C07D 401/12* (2006.01)

(52) U.S. Cl.
CPC ............... *C07F 5/05* (2013.01); *C07D 213/56* (2013.01); *C07D 401/12* (2013.01)

(58) Field of Classification Search
None
See application file for complete search history.

(56) References Cited

U.S. PATENT DOCUMENTS

| | | | | |
|---|---|---|---|---|
| 7,320,993 | B1 * | 1/2008 | Biedermann | C07D 213/56 514/344 |
| 7,842,278 | B2 | 11/2010 | Lee et al. | |
| 2008/0102026 | A1 | 5/2008 | Lee et al. | |

OTHER PUBLICATIONS

Brummond, et al.; Trimethylaluminum (TMA)-Catalyzed Reaction of Alkynyllithiums with Ethylene Oxide: Increased Yields and Purity of Homopropargylic Alcohols, Synlett (2005) No. 16, pp. 2457-2460.
Busso, et al.; Pharmacological Inhibition of Nicotinamide Phosphoribosyltransferase/Visfatin Enzymatic Activity Identifies a New Inflammatory Pathway Linked to NAD; PLoS ONE; (2008), vol. 3, Issue 5; pp. 1-10.

Gomez, et al.; A Simple Route to C-Monosubstituted Carborane Derivatives; J. Org. Chem. (1992) 57, pp. 1384-1390.
Hawthorne; The Role of Chemistry in the Development of Boron Neutron Capture Therapy of Cancer; Angew. Chem. Int. Ed. Engl. (1993) 32, pp. 950-984.
Mosmann; Rapid Colorimetric Assay for Cellular Growth and Survival: Application to Proliferation and Cytotoxicity Assays; J. Immunol. Meth. (1983) 65, pp. 55-63.
Stetter. et al.: Zur Kenntnis des Adamantyl-(1)-acetylens; Chem. Ber., (1962) 95, pp. 1039-1042.
Taylor, et al.; Further Intramolecular Diels-Alder Reactions of 1,2,4-Triazines. Synthesis of Dihydropyrrolo[2,3-b] Pyridines; Tetrahedron Letters, (1987) vol. 28, No. 4, pp. 379-382.
Taylor, et al; Intramolecular Diels-Alder Reactions of 1,2,4-Triazines. A General Synthesis of Furo[2,3-b] Pyridines, 2,3-Dihydor-Pyrano[2,3-b]Pyridines, and Pyrrolo[2,3-b]Pyridines, Tetrahedron, (1987) vol. 43, No. 21, pp. 5145-5158.
Todaro, et al.; The Initiation of Cell Division in a Contact-inhibited Mammalian Cell Line, J. Cell. Physiol. (1965) 66, pp. 325-333.
Beer, et al.; Preparation and Evaluation of Carborane Analogues of Tamoxifen; J. Med. Chem. (2010) 53, 8012-8020.
Busso, et al.; Pharmacological Inhibition of Nicotinamide Phosphoribosyltransferase/Visfatin Enzymatic Activity Identifies a New Inflammatory Pathway Linked to NAD; PLos ONE, (2008) vol. 3, Issue 5, pp. 1-10.
Campling, et al.; Use of the MTT Assay for Rapid Determination of Chemosensitivity of Human Leukemic Blast Cells; Leuk. Res. (1988) 12, 823-831.
Cigler, et al.; From Nonpeptide Toward Noncarbon Protease Inhibitors: Metallacarboranes as Specific and Potent Inhibitors of HIV Protease; Proc. Natl. Acad. Sci. USA (2005) 102, 15394-15399.
Crabtree, et al.; A New Intermolecular Interaction: Unconventional Hydrogen Bonds with Element—Hydride Bonds as Proton Acceptor; Acc. Chem. Res. (1996) 29, 348-354.
Endo, et al.; Potent estrogen agonists based on carborane as a hydrophobic skeletal structure A new medicinal application of boron clusters; Chemistry & Biology 8 (2001) 341-355.
Franfrlik, et al.; Interaction of Carboranes with Biomolecules: Formation of Dihydrogen Bonds; ChemPhysChem (2006) 7, 1100-1105.
Galli. et al.; Synthesis and Biological Evaluation of Isosteric Analogues of FK866, an Inhibitor of NAD Salvage; ChemMedChem (2008) 3, 771-779.
Hasmann, et al; FK866, a Highly Specific Noncompetitive Inhibitor of Nicotinamide Phophoribosyltransferase, Represents a Novel Mechanism for Induction of Tumor Cells Apoptosis; Cancer Res. (2003) 63; 7436-7442.

(Continued)

*Primary Examiner* — Timothy R Rozof
(74) *Attorney, Agent, or Firm* — Polsinelli PC

(57) ABSTRACT

The present invention relates to novel compounds, their use as anti-cancer agents and their synthesis. In particular, the compounds contain cluster boron moieties such as carborane or a borohydride and act as inhibitors for the enzyme Nampt. The biological properties of the inventive cluster boron compounds, in terms of biological inhibition and antiproliferative effect, are greater than other small molecule inhibitors of Nampt.

22 Claims, 15 Drawing Sheets
(9 of 15 Drawing Sheet(s) Filed in Color)

(56) References Cited

OTHER PUBLICATIONS

International Search Report and Written Opinion of the International Searching Authority: Feb. 8, 2013.

Issa, et al.; Boron in Drug Discovery: Carboranes as Unique Pharmacaphores in Biologically Active Compounds; Chem. Rev. (2011), 111, 5701-5722.

Julius, et al.; Synthesis and Evaluation of Transthyretin Amyloidosis Inhibitors Containing Carborane Pharmacophores; Proc. Natl. Acad. Sci. USA (2007) 104, 4808-4813.

Khan, et al; Molecular basis for the inhibition of human NMPRTase, a novel target for anticancer agents; Nature Structural & Molecular Biology (2006), vol. 13, No. 7, pp. 582-588.

Kim, et al.; Cancer's Molecular Sweet Tooth and the Warburg Effect; Cancer Res. (2006) 18, 8927-8930.

Laubengayer, et al.; The Dipole Moments of the Isomers of Dicarbadecaborane, B10H10C2H21; Inorganic Chemistry (1965), vol. 4, No. 10; pp. 1513-1514.

Lee, et al.; Carboranes Increase the Potency of Small Molecule Inhibitors of Nicotinamide Phosphoribosyltranferase; J. Med. Chem. (2012) A-E.

Liang, et al.; In vitro scratch assay: a convenient and inexpensive method for analysis of cell migration in vitro; Nature Protocols (2007) vol. 2, No. 2; 329-333.

Revollo, et al.; The NAD Biosynthesis Pathway Mediazted by Nicotinamide Phosphoribosyltransferase Regulates Sir2 Activiity in Mammalian Cells; J. Biol. Chem. (2004) 279, 50754-50763.

Scholz, et al.; Carbaboranes as Pharmacophores: Similarities and Differences Between Aspirin and Asborin; Eur. J. Med. Chem. (2011) 46, 1131.

Ujvary, et al.; Synthesis of (s)-3-(1-hydroxy-p-carboran-17-yl)alanine, a novel hydrophobic tyrosine-mimetic for peptides; Peptides (2002) 23; 795-799.

Valliant, et al.; The medicinal chemistry of carboranes; Coordination Chemistry Reviews (2002) 232; 173-230.

Yang, et al.; Nutrient-Sensitive Mitochondria! NAD+ Levels Dictate Cell Survival: Cell (2007) 130; 1095-1107.

Yoo, et al.; The First Stable Platinum (II) Complex of o-Carborane-linked Bipyridine as a Potential BNCT Reagent; Bull Korean Chem. Soc. (2005) vol. 26, No. 2; 231-232.

\* cited by examiner

SMALL MOLECULE INHIBITORS OF NICOTINAMIDE PHOSPHORIBOSYLTRANSFERASE (NAMPT)

CROSS-REFERENCE TO RELATED APPLICATIONS

This application claims priority to U.S. Provisional Application No. 60/629,877, filed Nov. 30, 2011, which is hereby incorporated by reference in its entirety.

FIELD

The present invention relates to novel compounds, their synthesis, and their use as anti cancer compounds. In particular, the compounds contain cluster boron moieties and act as inhibitors for the enzyme Nicotinamide Phosphoribosyltranferase (Nampt).

BACKGROUND

Over the past decade, there has been increasing interest in the use of cluster boron compounds as pharmacophoric units in drug design. For example, carboranes, which are icosahedral clusters comprised of boron, carbon, and hydrogen, demonstrate high chemical stability and may be incorporated into small molecules as analogs of aromatic hydrocarbons. Because each of the vertices of a cluster boron compound may be derivatized through substitution chemistry, these clusters may serve as rigid scaffolds upon which to build molecules with well-defined, three-dimensional conformations. In addition to hydrophobic interactions, it has been elucidated that carboranes bind strongly with biomolecules through a unique form of hydrogen bonding.

Nicotinamide Phosphoribosyltranferase is the first and rate limiting enzyme in the mammalian NAD$^+$ recycling pathway, converting nicotinamide to nicotinamide mononucleotide (NMN). Owing to the many disparate physiological roles and the cellular compartmentalization of NAD$^+$, this vital enzyme has been given different names (visfatin, pre-B cell colony enhancing factor (PBEF), NAmPRTase and Nampt). It has recently been shown that Nampt activity plays a central role in metabolism, cellular proliferation, cell survival, and inflammatory response, making this enzyme a new target for the treatment of many diseases, including cancer, Alzheimer's, diabetes and arthritis.

Very few compounds have been shown to have activity against Nampt. FK866 is one example, however, there remains a need to provide a new class of molecules able to modulate Nampt. Further, there remains a need for compounds with enhanced biological properties.

SUMMARY

In one aspect, the present disclosure provides a compound comprising Formula (I):

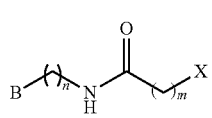

Formula (I)

wherein,
B is a cluster boron;
X is an aromatic moiety having one or more nitrogen atoms;
n is an integer ranging from 1 and 6, and where n is greater than 1, the resulting hydrocarbyl chain may be saturated or unsaturated; and
m is an integer ranging from 0 and 4, and where m is greater than 1, the resulting hydrocarbyl chain may be saturated or unsaturated.

In still another aspect, the present invention provides a method of producing a compound comprising Formula (I), the method comprising: (a) contacting a deprotonated cluster boron with an alkyl dihalide, to produce an alkyl halide substituted cluster boron compound; (b) contacting the alkyl halide substituted cluster boron with a nitrogen containing compound to produce the compound comprising Formula (II),

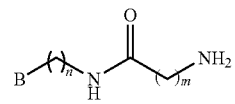

Formula (II)

and (c) contacting the compound comprising Formula (II) with a compound comprising Formula (III):

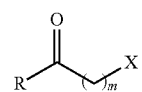

Formula (III)

wherein,
R is chosen from OH and Cl; and X, n, m and B are as described above for Formula (I) in the presence of a coupling agent or base to form the compound comprising Formula (I).

In still another embodiment, the present invention provides a process for producing the compound comprising Formula (I), wherein the compound comprising Formula (II) is contacted with the compound comprising Formula (III) in the presence of a coupling agent or base.

In yet another aspect, the invention provides a method of inhibiting Nampt in a subject, the method comprising administering a compound comprising Formula (I).

Other features and iterations of the disclosure are provided in more detail herein.

DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
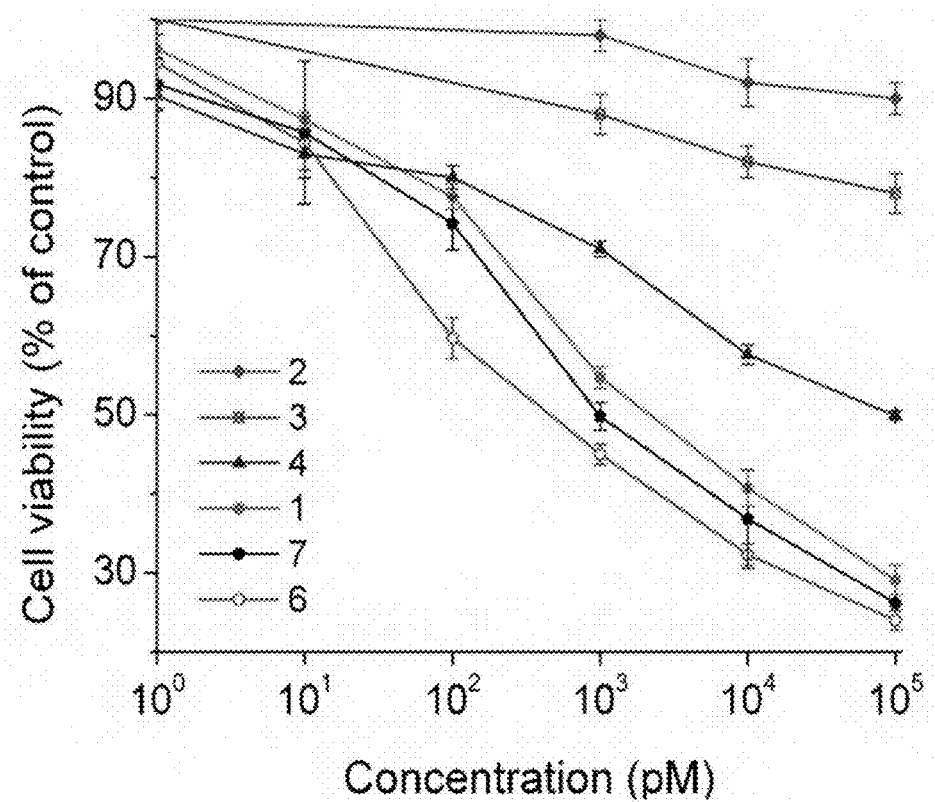
FIG. 1 shows the concentration dependent cell viability exhibited by (1)-(4), (6), (7) against the A549 human lung cancer cell line.

Briefly, the present invention relates to novel cluster boron compounds. In particular, the novel cluster boron compounds may be inhibitors of Nampt. The novel compounds contain a cluster boron group. The biological properties (for example, in terms of biological inhibition and antiproliferative effect) are greater than other small molecule inhibitors of Nampt. (I). Compositions (a) Compound Comprising Formula (I)

In one aspect, a compound comprising Formula (I) is provided:

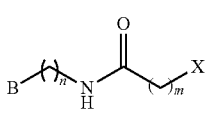

Formula (I)

wherein,
B is a cluster boron;
X is an aromatic moiety having one or more nitrogen atoms;
n is an integer ranging from 1 and 6, and where n is greater than 1, the resulting hydrocarbyl chain may be saturated or unsaturated; and
m is an integer ranging from 0 and 4, and where m is greater than 1, the resulting hydrocarbyl chain may be saturated or unsaturated.

B in the compound comprising Formula (I) represents a cluster boron compound. Cluster boron may be either an icosahedral boron (closo), or it may be a nido boron compound. For an icosahedral boron, the compound contains twelve vertexes which may be boron or carbon atoms. In some aspects, all vertices are boron atoms. As will be understood in the art, the valence of boron is such that the boron atoms making up the icosahedral structure may be bonded to a further substituent. Thus, the boron atoms may be bonded to one or more substituents, by way of non-limiting example, selected from hydrogen, hydrocarbyl, substituted hydrocarbyl, amino, amido, azo, esters, ethers, halogens, hydroxy, nitro, mercapto, phosphino, silyl, or sulfonated groups. In other embodiments, the icosahedral boron compound comprises one or more carbons in the icosahedral structure. Similarly, the carbon atoms comprising the icosahedral structure may be bonded to one or more additional substituents, these may be chosen from, for example, hydrogen, hydrocarbyl, substituted hydrocarbyl, amino, amido, azo, esters, ethers, halogens, hydroxy, nitro, mercapto, phosphino, silyl or sulfonated groups.

The nido compound has 11 vertexes. The nido compound may be substituted, by way of non-limiting example, with hydrogen, hydrocarbyl, substituted hydrocarbyl, amino, amido, azo, esters, ethers, halogens, hydroxy, nitro, mercapto, phosphino, or sulfonated groups similarly to the icosahedral compounds. Exemplary nido compounds include 7,8-, 7,9- and 2,9-C$_2$B$_9$H$_{12}^-$.

The incorporation of carbon into the cluster boron structure may occur at any vertex. For example, the cluster boron may contain 1, 2, 3, 4, 5, 6, 7, 8, 9, 10, or 11 carbon atoms in a twelve vertex compound, and 1, 2, 3, 4, 5, 6, 7, 8, 9, or 10 borons in an eleven vertex compound. Due to the three dimensional nature of the cluster boron compound, addition of more than one carbon in the cluster boron structure may create different structural isomers. For example, where two carbon atoms are present in the icosahedral structure the two carbon atoms may produce configurations described as ortho, meta, and para. In some preferred embodiments, the cluster boron is a carborane having two carbon atoms, wherein the carbon atoms are configured ortho to each other ([1,2-C$_2$B$_{10}$]), meta to each other ([1,7-C$_2$B$_{10}$]), or para ([1,12-C$_2$B$_{10}$]) to each other. When more than two carbon atoms are in the cluster boron, they can similarly be set in the cluster at any position without limitation.

The cluster boron is bound to the remainder of the compound comprising Formula (I) by a carbon-carbon bond or by a boron-carbon bond. This linkage can occur at any point on the icosahedral structure. In preferred embodiments, the linkage occurs through carbon atom vertexes.

The variable n is an integer ranging from 1 and 10, and where n is greater than 1, the resulting hydrocarbyl chain may be saturated or unsaturated. In some embodiments, the variable n is an integer ranging from 1 and 6. In various embodiments, n is equal to 1, 2, 3, 4, 5, or 6. In preferred embodiments, n is equal to 4 or 6. In some embodiments, the hydrocarbyl may contain one or more unsaturations along the chain. Where a double bond unsaturation occurs, the configuration of the double bond may be E or Z. In a preferred embodiment, the resulting hydrocarbyl chain is saturated.

The variable m is an integer ranging from 0 and 4, and where m is greater than 1, the resulting hydrocarbyl chain may be saturated or unsaturated. In some embodiments, m is zero and the amide functionality is connected directly to X. In other embodiments, m is greater than 1. In one embodiment, m is an integer ranging from 0 and 4. In other embodiments, m is 0, 1, 2, or 3. Where m is greater than 1, the hydrocarbyl may contain one or more unsaturations along the chain. Where a double bond unsaturation occurs, the configuration of the double bond may be E or Z. In a preferred embodiment, the resulting hydrocarbon chain is unsaturated with a E double bond.

The variable X is an aromatic moiety having one or more nitrogens. In preferred embodiments, there are 1, 2, or 3 nitrogens in the aromatic moiety. In some embodiments, the aromatic moiety is a 1-pyridyl, a 2-pyridyl, or a 3-pyridyl. In other embodiments, the aromatic moiety has two or more nitrogens which may be oriented in any position on the aromatic ring. In a preferred embodiment, the aromatic moiety is a 3-pyridyl moiety.

In one embodiment, the disclosure provides a compound comprising Formula (I)(a):

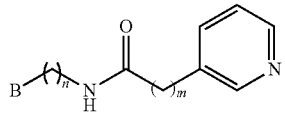

Formula (I)(a)

wherein,
B is a cluster boron;
n is an integer ranging from 1 and 6, and where n is greater than 1, the resulting hydrocarbyl chain may be saturated or unsaturated; and
m is an integer ranging from 0 and 4, and where m is greater than 1, the resulting hydrocarbyl chain may be saturated or unsaturated.

In one embodiment, the disclosure provides a compound comprising Formula (I)(b):

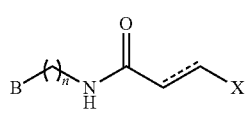

Formula (I)(b)

wherein,
B is a cluster boron;
n is an integer ranging from 1 and 6, and where n is greater than 1, the resulting hydrocarbyl chain may be saturated or unsaturated;
the dashed line represents a single or double bond; and
X is an aromatic moiety having one or more nitrogen atoms.

As discussed above, several isomers are possible within the compound comprising Formula (I). In some aspects of the present disclosure, a single isomer will be isolated, and in another aspect isomers may be mixed.

The compound comprising Formula (I) may be isolated in free form as salts. Preferably, the salt will be a pharmaceutically acceptable salt. Pharmaceutically acceptable salts include, without limitation, hydrochloride, hydrobromide, phosphate, sulfate, methanesulfonate, acetate, formate, tartaric acid, bitartrate, stearate, phthalate, hydroiodide, lactate, monohydrate, mucate, nitrate, phosphate, salicylate, phenylpriopionate, isobutyrate, hypophosphite, maleic, malic, citrate, isocitrate, succinate, lactate, gluconate, glucuronate, pyruvate, oxalate, fumarate, propionate, aspartate, glutamate, benzoate, terephthalate, and the like.

Exemplary compositions of the invention are shown and numbered in Table 1.

TABLE 1

Exemplary Compounds Comprising Formula (I)

TABLE 1-continued

Exemplary Compounds Comprising Formula (I)

37

[Structure of compound 37: a boron cluster connected via an alkyl chain to an amide linked to a pyridine ring]

In the above figures and herein ○=BH; ●=CH; and ✳=C.

(b). Pharmaceutical Compositions

In another aspect, the disclosure provides a pharmaceutical composition comprising the compound comprising Formula (I) and at least one pharmaceutically acceptable excipient. In various embodiments, one or more of the compounds described in section (I)(a) may be combined with at least one pharmaceutically acceptable excipient.

(i) excipient

A pharmaceutical compositions of the disclosure comprises at least one pharmaceutically acceptable excipient. Non-limiting examples of suitable excipients may include diluents, binders, fillers, buffering agents, pH modifying agents, disintegrants, dispersing agents, stabilizers, preservatives, and coloring agents. The amount and types of excipients may be selected according to known principles of pharmaceutical science.

In one embodiment, the excipient may include at least one diluent. Non-limiting examples of suitable diluents may include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose.

In another embodiment, the excipient may comprise a binder. Suitable binders may include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof.

In another embodiment, the excipient may include a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may comprise a buffering agent. Representative examples of suitable buffering agents may include, but are not limited to, MOPS, HEPES, TAPS, Bicine, Tricine, TES, PIPES, MES, Tris buffers or buffered saline salts (e.g., Tris buffered saline or phosphate buffered saline).

In various embodiments, the excipient may include a pH modifier. By way of non-limiting example, the pH modifying agent may be sodium carbonate or sodium bicarbonate.

In another alternate embodiment, the excipient may also include a preservative. Non-limiting examples of suitable preservatives may include antioxidants, such as alpha-tocopherol or ascorbate.

In a further embodiment, the excipient may include a disintegrant. Suitable disintegrants may include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth.

In yet another embodiment, the excipient may include a dispersion enhancer. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In a further embodiment, the excipient may include a lubricant. Non-limiting examples of suitable lubricants may include minerals such as talc or silica; and fats such as vegetable stearin, magnesium stearate or stearic acid.

In still another embodiment, it may be desirable to provide a coloring agent. Suitable color additives may include, but are not limited to, food, drug and cosmetic colors (FD&C), drug and cosmetic colors (D&C), or external drug and cosmetic colors (Ext. D&C).

The weight fraction of the excipient(s) in the composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The pharmaceutical composition may be mixed with one or more excipients to form a solid, liquid or cream dosage form. Methods of formulating a solid, liquid or cream dosage form are known in the art.

(ii) Optional Additional Pharmaceutical Ingredient

Optionally, the compound comprising Formula (I) may be combined with other compounds comprising Formula (I) or may be combined with one or more than one additional active pharmaceutical ingredients.

(II). Method of Making (a) Method for Producing a Compound Comprising Formula (I)

In another, alternative embodiment, the disclosure provides a method of making the compound comprising Formula (I):

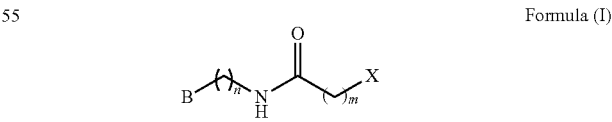

Formula (I)

wherein,
B is a cluster boron;
X is an aromatic moiety having one or more nitrogen atoms;
n is an integer between 1 and 6, and where n is greater than 1, the resulting hydrocarbyl chain may be saturated or unsaturated;

m is an integer between 0 and 4, and where n is greater than 1, the resulting hydrocarbyl chain may be saturated or unsaturated;

the method comprising, (a) contacting a deprotonated cluster boron with an alkyl dihalide, to produce an alkyl halide substituted cluster boron compound;

(b) contacting the alkyl halide substituted cluster boron with a nitrogen containing compound to produce the compound comprising Formula (II):

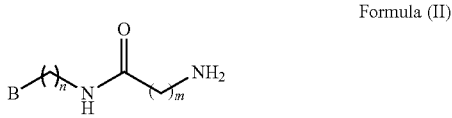

Formula (II)

wherein,

B is a cluster boron;

n is an integer ranging from 1 and 6, and where n is greater than 1, the resulting hydrocarbyl chain may be saturated or unsaturated; and m is an integer ranging from 0 and 4, and where m is greater than 1, the resulting hydrocarbyl chain may be saturated or unsaturated; and (c) contacting the compound comprising Formula (II) with a compound comprising Formula (III):

Formula (III)

wherein,

R is chosen from OH and Cl;

X is an aromatic moiety having one or more nitrogen atoms; and m is an integer ranging from 0 and 4, and where m is greater than 1, the resulting hydrocarbyl chain may be saturated or unsaturated in the presence of a coupling agent or a base to form the compound comprising Formula (I).

(i) Step (a)

B, X, n, and m for the compounds comprising Formula (I) are as described in section (I). In general, step (a) involves contacting a deprotonated cluster boron with an alkyl dihalide, to produce an alkyl halide substituted cluster boron compound. The cluster boron may be a cluster boron as described in section (I) which has been deprotonated in at least one position. Deprotonation can occur prior to contacting the deprotonated cluster boron with an alkyl dihalide for example by reaction with n-butyl lithium (n-BuLi) or another suitable base.

In some embodiments, the deprotonated cluster boron compound may be protected at one or more sites. For example, where the cluster boron is a carborane with more than one carbon atom, protecting groups can be used to provide selectivity to formation of the alkyl halide substituted cluster boron at one site or away from one site. In one embodiment, the protecting group may be a silyl protecting group. The protection reaction may occur prior to contacting with the alkyl dihalide. The protecting group may later be removed as is understood by one of skill in the art.

The alkyl dihalide is generally a hydrocarbyl moiety having two halide substitutents, typically on the terminal ends of a straight chain hydrocarbyl. Preferably, the halides are chosen form Cl, Br, and I. The alkyl dihalide may have from 1 to 6 carbon atoms, and the resulting hydrocarbyl may be saturated or unsaturated. In one preferred embodiment, the alkyl dihalide may be a 1-bromo-2-chloroethane, 1-bromo-3-chloropropane, 1-bromo-4-chlorobutane, 1-bromo-5-chloropentane, or 1-bromo-6-chlorohexane.

(ii) Step (b)

The alkyl substituted cluster boron formed in step (a) may be reacted to give the compound comprising Formula (II). The variables for the compound comprising Formula (II) are as described for Formula (I) in section (I). In some embodiments, the compound comprising Formula (II) is protonated at the terminal amine position to form an —NH$_3$ cation or salt.

Step (b) involves reaction of the alkyl halide substituted cluster boron with a nitrogen containing compound to facilitate introduction of the nitrogen in place of the halide. The nitrogen atom may be substituted in a variety of ways. In some embodiments, the alkyl halide substituted cluster boron is reacted with a compound chosen from a phthalimide, an azide or is a protecting ammonia compound such as Boc$_2$NH to give an intermediate nitrogen containing compound which is then reduced to give the compound comprising Formula (II).

In such embodiments, reduction may be accomplished by a variety of agents. Suitable reducing agents include borohydride reagents (such as sodium borohydride) and aluminum hydrides, hydrazines, and hydrogenation regents. Hydrogenation reagents may be chosen from transition metals, for example, ruthenium, iridium, palladium, platinum, or rhodium. In one embodiment, where the nitrogen containing compound is a phthalimide, the reduction may occur from a hydrazine reduction. In another embodiment, where the nitrogen containing compound is an azide, the reduction may be accomplished by a Palladium(0) source such as palladium on carbon.

(iii) Step (c)

The compound comprising Formula (II) may be contacted with a compound comprising Formula (III) to form the compound comprising Formula (I). The reaction, in general, is facilitated by a coupling agent or a base. The compound comprising Formula (III) may be referred to as a carboxylic acid or acyl chloride depending on the identity of R which is chosen from OH and Cl. X is as described in section (I).

The compound comprising Formula (III) is generally a short chain carboxylic acid or acyl chloride. Exemplary, but non limiting, examples of compounds comprising Formula (III) are shown in TABLE 2, and in each case R is chosen from OH and Cl. In exemplary embodiments, the compound comprising Formula (III) are (E)-3-(3'-pyridyl)acrylic acid or (E)-3-(pyridine-3-yl)acryloyl chloride.

TABLE 2

Exemplary Compounds Comprising Formula (III)

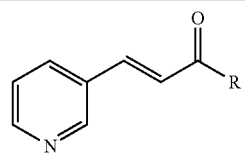

TABLE 2-continued

Exemplary Compounds Comprising Formula (III)

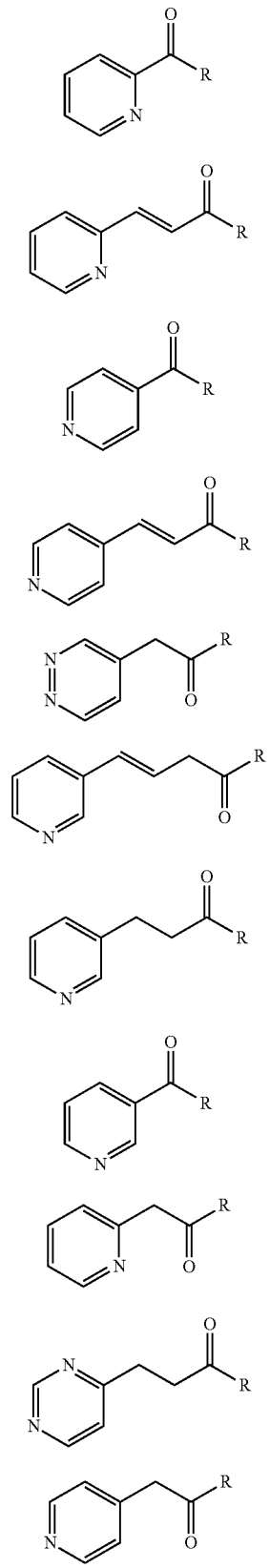

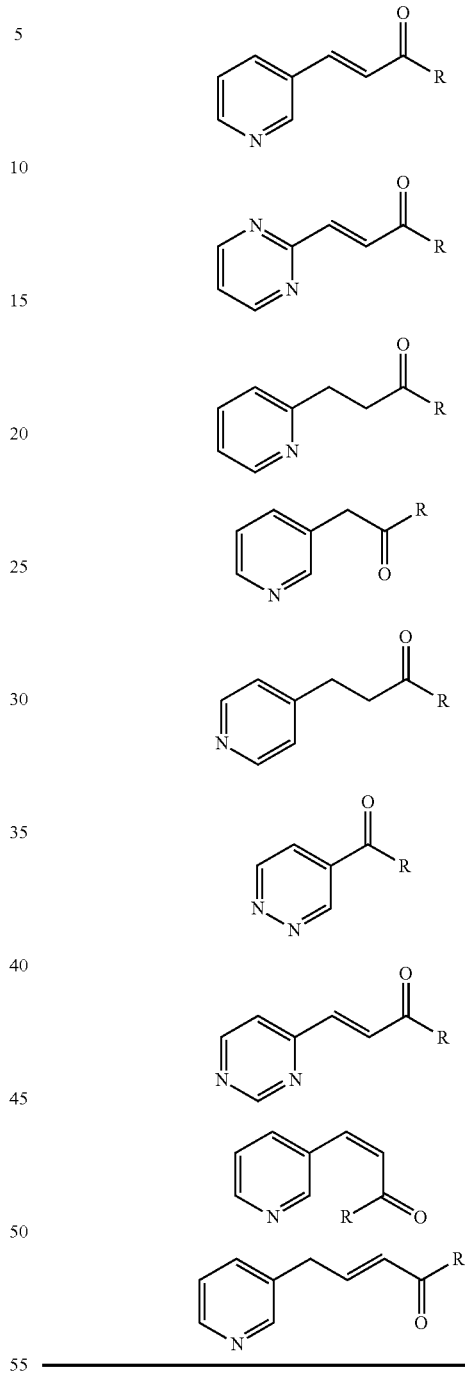

The mole to mole ratio of the compound comprising Formula (II) to the compound comprising Formula (III) can range over different embodiments of the invention. In one embodiment, the ratio of the compound comprising Formula (II) to the compound comprising Formula (III) varies from about 0.9:1 to about 1:10. In some embodiments, the mole to mole ratio of the compound comprising Formula (II) to the compound comprising Formula (III) is about 1:1 to about 1:1.5. In various embodiments, the mole to mole ratio of the compound comprising Formula (II) to the compound comprising Formula (III) is about 1:1, about 1:1.1, about 1:1.2, about 1:1.3, about 1:1.4, or about 1:1.5. In an exemplary embodiment, the mole to mole ratio of the compound comprising Formula (II) to the compound comprising Formula (III) is 1:1.

The reaction is preferably carried out in a solvent and is more preferably carried out in an organic solvent. The solvent may be chosen without limitation from including alkane and substituted alkane solvents (including cycloalkanes) alcohol solvents, halogenated solvents, aromatic hydrocarbons, esters, ethers, ketones, and combinations thereof. Non-limiting examples of suitable organic solvents are acetonitrile, acetone, allyl alcohol, benzene, butyl acetate, chlorobenzene, chloroform, chloromethane, cyclohexane, cyclopentane, dichloromethane (DCM), dichloroethane, diethyl ether, dimethoxyethane (DME), dimethylformamide (DMF), dimethyl sulfoxide (DMSO), dioxane, ethanol, ethyl acetate, ethylene dichloride, ethylene bromide, formic acid, fluorobenzene, heptane, hexane, isobutylmethylketone, isopropanol, isopropyl acetate, N-methylpyrrolidone, methanol, methylene bromide, methylene chloride, methyl iodide, methylethylketone, methyltetrahydrofuran, pentyl acetate, propanol, n-propyl acetate, sulfolane, tetrahydrofuran (THF), tetrachloroethane, toluene, trichloroethane, water, xylene and combinations thereof. In exemplary embodiments, the solvent is dimethylformamide or tetrahydrofuran.

An additional proton acceptor may be added to facilitate the reaction. The proton acceptor generally has a pKa greater than about 7, or from about 7 to about 13, or more preferably from about 8 to about 10. Representative proton acceptors include, but are not limited to, borate salts (such as, for example, $NaBO_3$), di- and tri-basic phosphate salts, (such as, for example, $Na_2HPO_4$ and $NaPO_4$), bicarbonate salts, carbonate salts, hydroxides, alkoxides, (including methoxide, ethoxide, propoxide, butoxide, and pentoxide, including straight chain and branched), and organic proton acceptors, (such as, for example, pyridine, triethylamine, N-methylmorpholine, and N,N-dimethylaminopyridine), and mixtures thereof. In some embodiments, the proton acceptor may be stabilized by a suitable counterion such as lithium, potassium, sodium, calcium, magnesium, and the like. In one preferred embodiment, the proton acceptor is triethylamine.

The amount of the proton acceptor which is added may vary. Generally, the proton acceptor is added in excess to the compound comprising Formula (II). In some embodiments, the mole to mole ratio of the compound comprising Formula (II) to the proton acceptor can range from about 1:1.1 to about 1:20. In some embodiments, the mole to mole ratio of the compound comprising Formula (II) to the proton acceptor is about 1:2, about 1:3, about 1:4, about 1:5, about 1:6, about 1:7, about 1:8, about 1:9, or about 1:10. In one preferred embodiment, the mole to mole ratio of the compound comprising Formula (II) to the proton acceptor is 1:3.

A coupling agent may facilitate the reaction. Suitable coupling agents may be chosen from benzotriazole-1-yl-oxy-tris-(dimethylamino)-phosphonium hexafluorophosphate, N,N'-Dicyclohexylcarbodiimide, O-(7-azabenzotriazol-1-yl)-N,N,N',N'-tetramethyluronium hexafluorophosphate, benzotriazol-1-yl-oxytripyrrolidinophosphonium hexafluorophosphate, and 1-ethyl-3-(3-dimethylaminopropyl) carbodiimide. In a preferred embodiment, the coupling agent is benzotriazole-1-yl-oxy-tris-(dimethylamino)-phosphonium hexafluorophosphate. In other embodiments, a proton acceptor facilitates the reaction. Suitable proton acceptors include, but are not limited to organic bases such as alkyl amines, for example triethylamine, trimethylamine, or N,N-diisopropylethylamine, or N-heterocyclic compounds such as pyridines or DABCO®. In one preferred embodiment, the base is N,N-diisopropylethylamine.

The amount of time over which the reaction is conducted may also vary within various embodiments. In some embodiments, the reaction may be conducted over a period of 8 hours to 1 day. In particular embodiments, the reaction is carried out for about 8 hours, about 9 hours, about 10 hours, about 11 hours, about 12, about 13 hours, about 14 hours, about 15 hours, about 16 hours, about 17 hours, or about 18 hours. In preferred embodiments, the reaction is conducted for about 12 hours.

The temperature may vary over different embodiments, in some embodiments the temperature may range from about 15° C. to about 40° C. In particular embodiments the temperature may range from about 15° C. to about 25° C., from about 20° C. to about 30° C., from about 25° C. to about 30° C. In preferred embodiments the temperature may be about 20° C., about 21° C., about 22° C., about 23° C., about 24° C., about 25° C., about 26° C., about 27° C., about 28° C., about 29° C., or about 30° C.

In general, the reaction may be carried out in an inert atmosphere such as argon, nitrogen, or a similar inert atmosphere. Suitable apparatus for maintaining an inert atmosphere may be used to facilitate performing the reaction under an inert atmosphere.

Steps (a)-(c) may have an overall yield of at least about 40%. In still another embodiment, the yield of the compound comprising Formula (I) may be greater than about 45%, about 50% or about 55%. The compositions may be purified by methods known in the art including crystallization, chromatography, filtration and the like. In preferred embodiments, the compound comprising Formula (I) is isolated by a biphasic extraction and the solvent is removed by evaporation. The purified isolated yield may similarly be greater than about 45%, about 50% or about 55%.

(b) Method of Producing a Compound Comprising Formula (I) from a Compound Comprising Formula (II)

In still another embodiment, the present disclosure provides method a for making a compound comprising Formula (I),

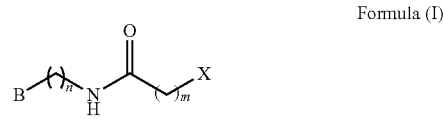

Formula (I)

wherein,

B is a cluster boron;

X is an aromatic moiety having one or more nitrogen atoms;

n is an integer ranging from 1 and 6, and where n is greater than 1, the resulting hydrocarbyl chain may be saturated or unsaturated; and m is an integer ranging from 0 and 4, and where m is greater than 1, the resulting hydrocarbyl chain may be saturated or unsaturated;

wherein the method comprises contacting a compound comprising Formula (II):

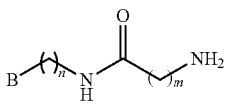

Formula (II)

wherein,
B is a cluster boron;
n is an integer ranging from 1 and 6, and where n is greater than 1, the resulting hydrocarbyl chain may be saturated or unsaturated; and
m is an integer ranging from 0 and 4, and where m is greater than 1, the resulting hydrocarbyl chain may be saturated or unsaturated.
with a compound comprising Formula (III):

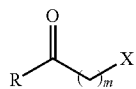

Formula (III)

wherein,
R is chosen from OH and Cl;
X is an aromatic moiety having one or more nitrogen atoms; and
m is an integer ranging from 0 and 4, and where m is greater than 1, the resulting hydrocarbyl chain may be saturated or unsaturated
in the presence of a coupling agent or a base.

The compound comprising Formula (I) is described in section (I) and the compounds comprising Formulas (II) and (III) are as described in section (II)(a). The reaction may be facilitated as described in section (II)(a). Suitable coupling agents are listed in section (II)(a).

The yield of the reaction between the compound comprising Formula (II) and Formula (III) can and will vary. In some embodiments, the yield may be at least about 80%. In still another embodiment, the yield of the compound comprising Formula (I) may be greater than about 85%, about 90% or about 95%. In still another embodiment, the yield may be about 95%. The compositions may be purified by methods known in the art including crystallization, chromatography, filtration and the like. In preferred embodiments, the compound comprising Formula (I) is isolated by a biphasic extraction and the solvent is removed by evaporation. The purified isolated yield may similarly be greater than about 85%, about 90% or about 95%.

(III). Method of Using

In yet another aspect, the disclosure provides a method of inhibiting Nampt in a subject, the method comprising administering a subject a compound comprising Formula (I),

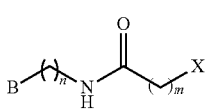

Formula (I)

wherein,
B is a cluster boron;
X is an aromatic moiety having one or more nitrogen atoms;

n is an integer ranging from 1 and 6, and where n is greater than 1, the resulting hydrocarbyl chain may be saturated or unsaturated; and
m is an integer ranging from 0 and 4, and where m is greater than 1, the resulting hydrocarbyl chain may be saturated or unsaturated.

The variables B, n, m, and X may be as described in section (I).

Administration of a compound comprising Formula (I) may act to inhibit the enzyme Nampt. Thus, it will be understood by the skilled artisan that the variety of conditions that the compounds may be useful in treating are those associated with, or which may be alleviated by, modification of Nampt function. The compositions may be used to treat a conditions including cancer (including, but not limited to, colorectal, breast, prostate, brain, pancreatic, lung, gastric, fibrosarcoma, lymphoma, leukemia, and liver), arthritis, diabetes, Huntington's disease, Alzheimer's, inflammation, neurodegeneration, spinal cord injury, and the like.

The compounds described in section (I) may show enhanced inhibition over FK866. In some embodiments, inhibition is 50× greater than that by FK866. In other embodiments, inhibition is 100× greater, 200× greater, or 500× greater than that by FK866.

The compounds may be administered to the subject by a variety of routes. For example, a compound comprising Formula (I) may be administered orally (via a solid or liquid dosage form), parenterally (i.e., subcutaneously, intradermally, intravenously, intramuscularly, intracranially, or intraperitoneally), or topically (i.e., transdermally or transmucosally).

Suitable subjects include, without limit, humans, as well as companion animals such as cats, dogs, rodents, and horses; research animals such as rabbits, sheep, pigs, dogs, primates, mice, rats and other rodents; agricultural animals such as cows, cattle, pigs, goats, sheep, horses, deer, chickens and other fowl; zoo animals; and primates such as chimpanzees, monkeys, and gorillas. In a preferred embodiment, the subject may be a human.

The compounds may be administered in saline or with a pharmaceutically acceptable excipient as described in section (I). The amount of the compound which is administered to the subject may depend on the subject and the route of administration and may be determined by a person of ordinary skill in the art.

Administration of the compounds described in section (I) also results in low $IC_{50}$ values in comparison to FK866. $IC_{50}$ values are the half maximal inhibitory concentration, which measures the effectiveness of a compound in biological inhibition. In some embodiments, the $IC_{50}$ values for the compounds described in section (I) are 30% to 90% decreased when compared to FK866. In various embodiments, the compounds of the invention are 30%, 40%, 50%, 60%, 70%, 80%, 90%, or 100% decreased when compared to FK866.

Administration of the compounds described in section (I) coincides with a high cancer cell antiproliferative effect when compared to FK866. In some embodiments, the antiproliferative effect of the compound comprising Formula (I) is 5× greater than that of FK866. In other embodiments, the antiproliferative effect of the compound comprising Formula (I) is 10× greater than that of FK866, and in still other embodiments, the antiproliferative effect of the compound comprising Formula (I) is 25× greater than that of FK866.

DEFINITIONS AND ABBREVIATIONS

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

A549 (Ademnocarcinomic human alveolar basal epithelial cells (lung)

The term "acyl," as used herein alone or as part of another group, denotes the moiety formed by removal of the hydroxyl group from the group COOH of an organic carboxylic acid, e.g., RC(O)—, wherein R is $R^1$, $R^1O$—$R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (0), e.g., RC(O)O— wherein R is as defined in connection with the term "acyl."

The term "allyl," as used herein not only refers to compound containing the simple allyl group ($CH_2$=CH—$CH_2$—), but also to compounds that contain substituted allyl groups or allyl groups forming part of a ring system.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkoxide" or "alkoxy" as used herein is the conjugate base of an alcohol. The alcohol may be straight chain, branched, cyclic, and includes aryloxy compounds.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

BOC or Boc as used herein refers to the t-butyloxycarbonyl protecting group.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

DLD1 refers to Human Colon Carcinoma Cells.

The terms "halide" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thiol.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

PANC1 refers to Human Pancreatic Carcinoma.

PC3 refers to Human Prostate Cancer Cells.

U87 refers to Human glioblastoma-astroncytoma (brain).

T47D refers to Human Ductal Breast Epithelial Tumor Cells.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

EXAMPLES

General Information

Visual depictions of the compounds are provided in TABLE 3. The Examples herein refer to these compounds the number associated with the compounds in the table. For the compounds ○=BH; ●=CH; and *=C.

TABLE 3

| Compound Reference |
|---|
| (1) FK866 |
| (2) |
| (3) PH4-PPEA $C_{18}H_{20}N_2O$ |
| (4) ADM-PPEA $C_{22}H_{26}N_2O$ |
| (5) OC4-PPEA $C_{14}B_{10}H_{26}N_2O$ |
| (6) MC4-PPEA $C_{14}B_{10}H_{26}N_2O$ |
| (7) PC4-PPEA $C_{14}B_{10}H_{26}N_2O$ |

TABLE 3-continued

Compound Reference

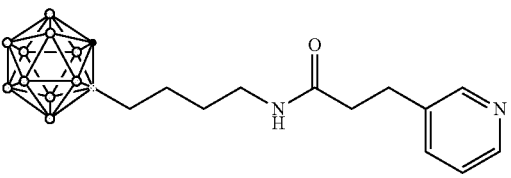

OC4-PPAA
$C_{14}B_{10}H_{28}N_2O$ (33)

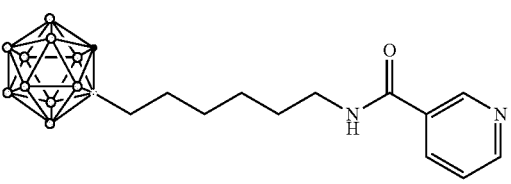

OC6-NIC
$C_{14}B_{10}H_{28}N_2O$ (34)

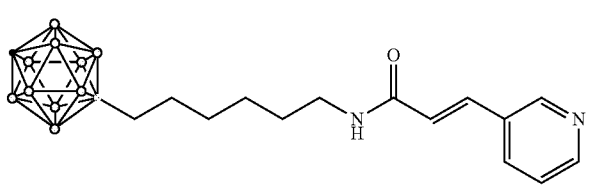

OC6-PPEA
$C_{16}B_{10}H_{32}N_2O$ (35)

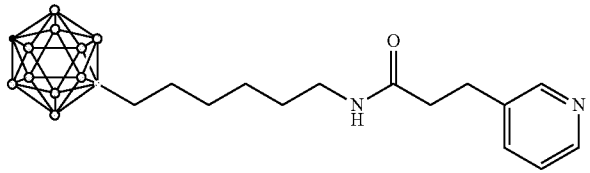

OC6-PPAA
$C_{16}B_{10}H_{32}N_2O$ (36)

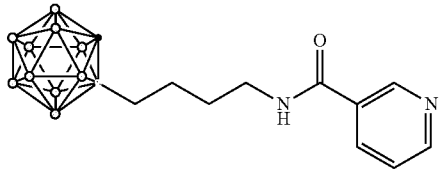

OC4-NIC
$C_{12}B_{10}H_{24}N_2O$ (37)

Reaction Conditions and Chemicals

All manipulations were performed under an inert atmosphere. Chemicals were handled by using a combination of Schlenk, vacuum-line, and glovebox techniques. THF was distilled from sodium benzophenone ketyl under argon. Silica gel (60 Å, 63-200 μm) was obtained from Sorbent Technologies (Norcross, Ga.). The carboranes and decaborane were purchased from Katchem spol. Sr.o. (Prague, CZ). Bulk solvents and celite were purchased from Fischer Scientific (Waltham, Mass.) and were used as received. Anhydrous solvents were purchased from Aldrich (St. Louis, Mo.). Tert-butyldimethylsilyl-o-carborane, o-$[C_2B_{10}H_{11}]SiMe_2$t-Bu, was prepared using the method described previously as in F. A. Gomez, M. F. Hawthorne, *J. Org. Chem.* 1992, 57, 1384-1390.

Analytical Instrumentation

NMR spectra were recorded on Bruker DRX300, DRX500, Avance-400 and Avance-500 instruments. Chemical shifts (δ, ppm) for $^1H$ and $^{13}C$ were referenced to residual solvent peaks. Boron chemical shifts were externally referenced to $BF_3.OEt_2$ in $CDCl_3$.

Infrared spectra (IR) were recorded on a Nicolet Nexus 470. Spectra were measured using KBr pellets. Absorption bands are given in wavenumbers ($cm^{-1}$).

High Resolution Mass spectra (HR-MS) were obtained using a Waters Q-Tof API-US, ABI QSTAR and ABI Mariner o-TOF Biospectrometry Workstation. Data reported as follows: (m/z: calculated; m/z: found). The isotopic distribution of each carborane containing ion matched that expected for normal abundance boron.

Synthesis and Characterization

General Procedure: Compounds (2)-(7) were synthesized by the coupling of trans-3-(3'-pyridyl)acrylic acid with the respective amines by the following general procedure. The substituted amine, or ammonium chloride and trans-3-(3'-pyridyl)acrylic acid was dissolved in DMF (10-15 mL) to which the coupling reagent BOP was added. The reaction mixture was allowed to stir at room temperature overnight, after which it was quenched by the addition of water (20 mL) and ethyl acetate (20 mL). The biphasic mixture was transferred to a separatory funnel and the organic layer was removed. The aqueous layer was twice extracted with 20 mL of ethyl acetate and the combined organic fractions were washed with 20 mL of water and 3 mL of brine. The organic layer was dried with anhydrous $Na_2SO_4$ and the solvent removed under vacuum. Before testing, compounds (2)-(7) were purified by RP-HPLC on a Phenomenex Luna C(2)18 column (150×4.6 mm) using a Beckman System Gold instrument running 32-Karat software. After purification, the purity of each test agent was greater than 95%.

Example 1

Biological Assays

Cell Lines and Reagents

A549, DLD1, T47D and PC3 were purchased from ATCC (Manassas, Va.). MTT assay kit was purchased from Promega (Madison, Wis.). FK866 and NMN were purchased from Enzo Life Sciences (Farmingdale, N.Y.) and Sigma (St Louis, Mo.) respectively.

MTT Assay

MTT assay provides a direct measure of mitochondrial activity which can be compared directly with previously reported numbers of (1) by Hasmann (Hasmann, M.; Schemainda, I. FK866, a highly specific noncompetitive inhibitor of nicotinamide phosphoribosyltransferase, represents a novel mechanism for induction of tumor cell apoptosis. *Cancer Res.* 2003, 63, 7436-7442.) The results are shown in FIG. 1, which shows the concentration-response curves against A549 cell line. For clarity (5) was omitted from the graph but displayed results between 1 and 7. Additional MTT assays are show in FIGS. 11(A)-(D) and FIG. 12 for compounds (33)-(37).

Rescue Assay

Figure 2:
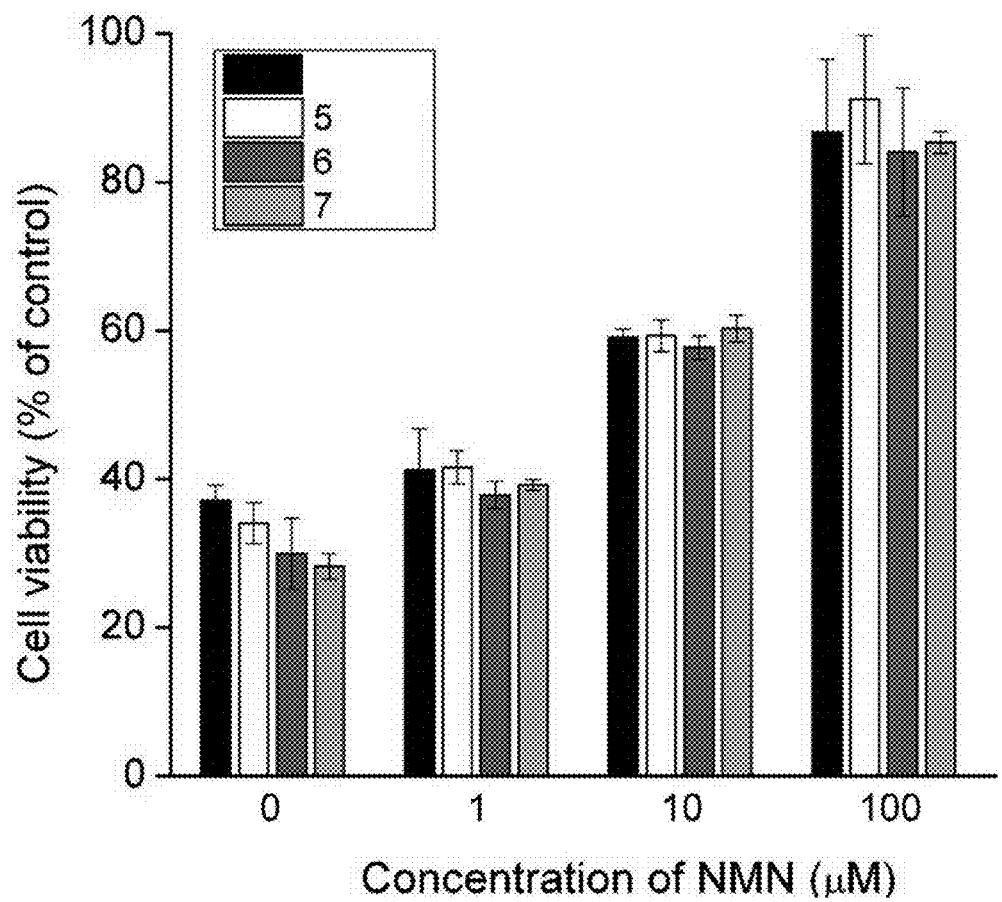
FIG. 2 shows the concentration-dependent cell rescue. A549 cells were treated with 10 nM (1), (5), (6), or (7). Error bars represent the mean±SD. Cell viability was measured using the MTT assay. Each measurement was repeated 4 times. A nearly complete rescue of the cells was afforded with increasing concentrations.

Cell rescue assays were conducted using Nicotinamide Mononucleotide (NMN) as described by Busso et al. (Busso, N.; Karababa, M.; Nobile, M.; Rolaz, A.; Van Gool, F.; Galli, M.; Leo, O.; So, A.; De Smedt, T. Pharmacological inhibition of nicotinamide phosphoribosyltransferase/visfatin enzymatic activityidentifies a new inflammatory pathway linked to NAD. PLoS One 2008, 21, e2267.) Briefly, A549 and DLD1 cells were plated at a density of 10,000 cells per well in 96 well plates for overnight. Cells were then treated with 10 nM concentrations of agents (1), (5)-(7). Simultaneously, concentrations of 1, 10 or 100 μM NMN were added to the cultures. Cultures were then continued for 72 h. MTT reagent was added to the cells after 72 h for a period of 3 h and then MTT crystals were solubilized using solubilization buffer. Readings were taken at 570 nm wavelength. Control cells were considered as 100% survival to plot the inhibition and rescue graph. The experiments were repeated four times. Results are shown in FIG. 2.

Recombinant Nampt Inhibition Assay

Figure 3:
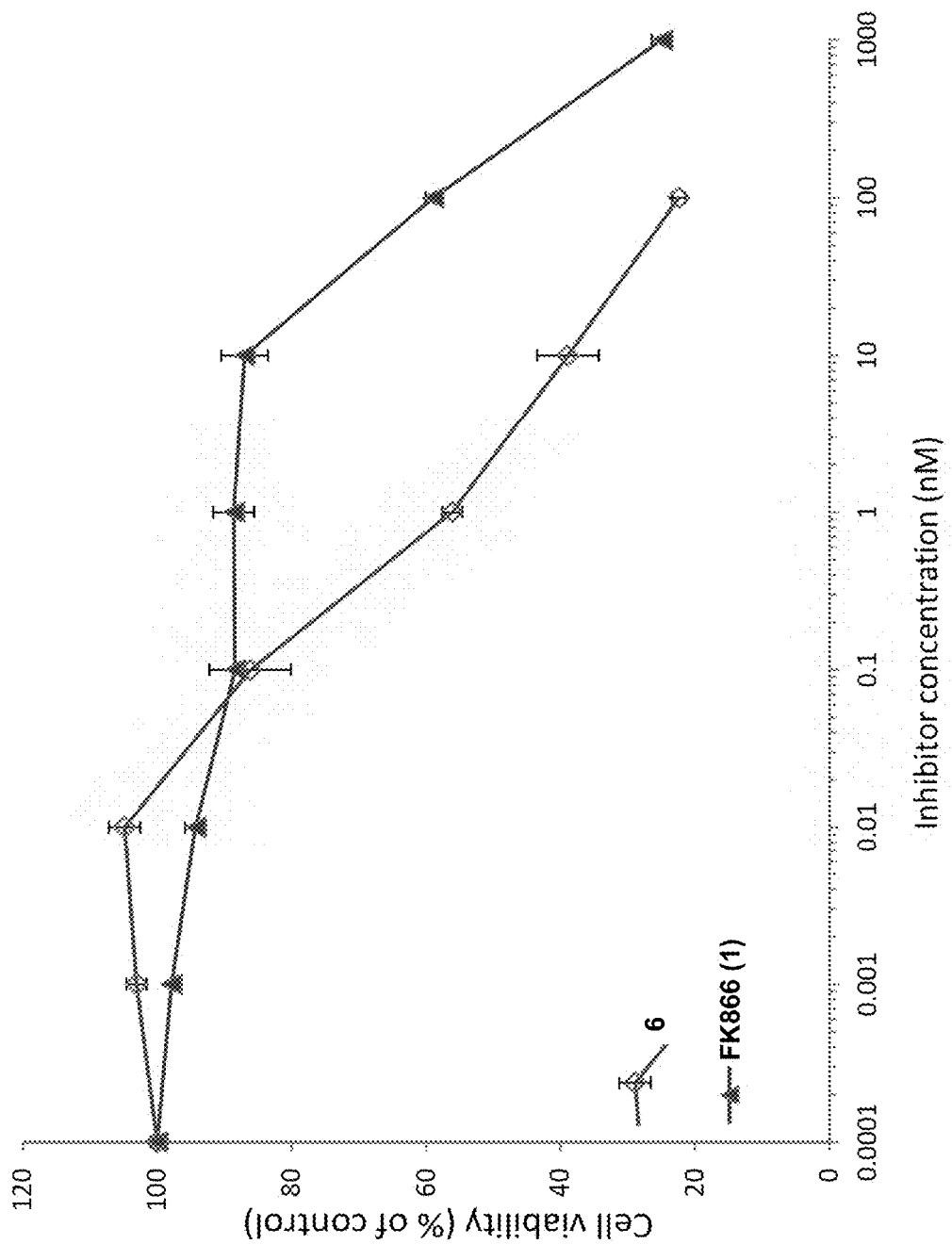
FIG. 3 shows recombinant Nampt inhibition for FK866 against compound (6).

The assay was performed according to the manufacturers protocol (CycLex NAMPT Colorimetric Assay Kit, MBL International Corp., Woburn, Mass.). The NAMPT assay was performed according manufacturers protocol. Briefly we used the "1-Step Assay Method" for which following reagents were mixed to make assay buffer and kept at ice before starting the assay: 10 μL each of 10× Nampt assay buffer, nicotinamide, PRPP, ATP and EtOH; 2 μL each of recombinant NMNAT1, WST-1, ADH, diaphorase and $D_2O$. The Nampt inhibition assay was performed by mixing 2 μl of various concentrations (to make 1 pM-100 nM) of FK866 or (6) (or 2 μL DMSO as vehicle control) with the following: 2 μL recombinant Nampt and 36 μL $D_2O$. The reaction was initiated by adding 60 μL of 1-Step Assay Buffer to each well and mixed thoroughly followed by incubation at 30° C. for 20 mins. After this period, the absorbance at 450 nm was measured and compared with the positive control. FIG. 3 shows recombinant Nampt inhibition for FK866. TABLE 4 lists measured Half-Maximal Inhibitory Concentrations ($IC_{50}$) against Human Tumor Cell Lines A549 (Lung), DLD1 (Colon), and T47D (Breast).

TABLE 4

Measured Half-Maximal Inhibitory Concentrations ($IC_{50}$)

| | IC50 (nM) | | |
|---|---|---|---|
| Compound | A549 | DLD1 | T47D |
| 1 | 1.62 ± 0.04 | 3.14 ± 0.11 | 3.20 ± 0.16 |
| 4 | 88.9 ± 1.1 | 20.3 ± 0.44 | 186.4 ± 4.1 |
| 5 | 0.92 ± 0.02 | 1.69 ± 0.06 | 1.29 ± 0.13 |
| 6 | 0.41 ± 0.01 | 0.31 ± 0.01 | 0.32 ± 0.02 |
| 7 | 0.99 ± 0.03 | 2.20 ± 0.12 | 0.58 ± 0.03 |

Example 2

Synthesis of trans-N-butyl-3-(3'-5pyridyl)acrylamide (2)

Compound 2 was prepared and isolated by reacting butylamine (0.3 mL, 3.04 mmol) with trans-3-(3'-pyridyl)acrylic acid (302 mg, 2.02 mmol), and BOP (893 mg, 2.02 mmol) in dimethylfonnamide (14 mL). The reaction was allowed to stir overnight to yield yellow oil (70 mg, 18%). $^1$H NMR (500 MHz, $CD_3OD$, J=Hz): δ 8.64 (1H, s, br, $H_{arom}$), 8.45 (1H, s, br, $H_{arom}$), 7.97 (1H, d, J 8.0, $H_{arom}$), 7.47 (1H, d, $J_{trans}$=15.5, CH=CH), 7.40 (1H, m, $H_{arom}$), 6.65 (1H, d, $J_{trans}$=15.5, CH=CH), 3.28 (2H, m, $CH_2NH$), 1.48 (2H, m, $CH_3CH_2$), 1.33 (2H, m, $CH_3CH_2CH_2$), 0.89 (3H, t, J 6.0, $CH_3$). $^{13}$C NMR (125.8 MHz, $CD_3OD$): δ 167.7 (C=O), 150.7, 149.7, 137.3, 136.3, 133.0, 125.6, 124.9 ($C_{arom}$+CH=CH), 40.4 ($CH_2NH$), 32.5 ($CH_3CH_2$), 21.1 ($CH_2CH_2NH$), 14.1 ($CH_3$). HRMS (TIS, pos) for $NaC_{12}H_{16}N_2O$ (m/z): calcd 227.1160 (M+Na)$^+$. found 227.2181.

Example 3

Synthesis of trans-N-(4'-phenylbutyl)-3-(3"-pyridyl)acrylamide (3)

Compound (3) was prepared and isolated by reacting 4-phenylbutylamine (1 mL, 6.21 mmol) with trans-3-(3'-pyridacrylic acid (617 mg, 4.14 mmol), and BOP (1829 mg, 4.14 mmol) in dimethylformamide (12 mL). The reaction was allowed to stir overnight to yield a pale yellow oil (630 mg, 60%). $^1$H NMR (500 MHz, $CD_2Cl_2$ J Hz): δ 8.71 (1H, s, br, $H_{arom}$), 8.63 (1H, s, br, $H_{arom}$), 7.77 (1H, m, $H_{arom}$), 7.58 (1H, d, $J_{trans}$=16.0, CH=CH), 7.22 (6H, m, $H_{arom}$) 6.90 (1H, s, br, O=CNH), 6.63 (1H, d, $J_{trans}$=15.5, CH=CH), 3.39 (2H, m, CH$_2$NH), 2.63 (2H, m, C$_6$H$_5$CH$_2$), 1.64 (4H, m, CH$_2$). $^{13}$C NMR (125.8 MHz, CD$_2$Cl$_2$): 5165.5 (C=O), 150.4, 149.4, 142.6, 136.7, 134.5, 131.2, 128.7, 128.6, 126.0, 124.0, 123.9 (C$_{arom}$, +CH=CH), 39.9 (CH$_2$NH), 35.8 (C$_6$H$_5$CH$_2$), 29.6, 29.2 (CH$_2$). HRMS (TIS, pos) for NaC$_{18}$H$_{20}$N$_2$O (m/z): calcd 303.1473 (M+Na)$^+$. found 303.2519.

Example 4

Synthesis of trans-N-(3'-(1''-adamantyl)-2'-propyn-1'-yl)-3-(3''-pyridyl)acrylamide (4)

Figure 4:
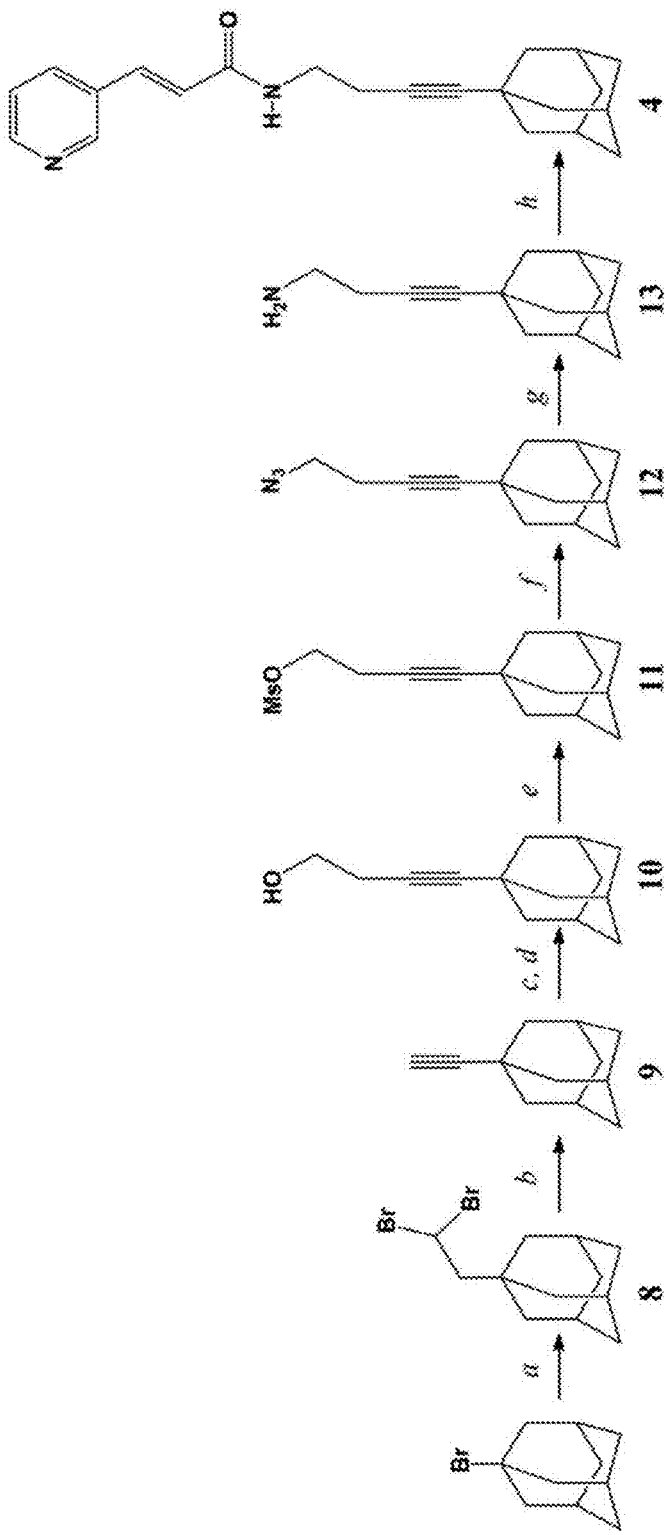
FIG. 4 shows a synthetic route to compound (4). Reagents and conditions: a) AlBr$_3$, CH$_2$CHBr, 4 h at −65° C.; b) KO$^t$Bu, THF, 4-5 d rt; c) $^n$BuLi, THF, 2 h at −65° C.; d) AlMe$_3$, (CH$_2$)$_2$O, THF, 2d rt; e) Et$_3$N, MsCl, Et$_2$O, 4 h rt; f) NaN$_3$, DMF, 3 h refluxing; g) LiAlH$_4$; THF, 3 h, rt; h) DMF, BOP, Et$_3$N, C$_5$NH$_4$(CH)$_2$COOH, overnight rt.

To introduce a butylamine moiety to adamantane, we first prepared 1-ethynyladamantane according to the scheme depicted in FIG. 4. Following the previously reported methods, we successfully synthesized 1-(2,2-dibromoethynyl)adamantane (8). However, the subsequent dehydrobromination step was modified to use potassium tert-butoxide in tetrahydrofuran at room temperature instead of suggested potassium hydroxide reflux in diethylene glycol. Due to high volatility of 1-ethynyladamantane (9), the use of low reaction temperature was preferred and it resulted in high (91%) and reproducible yield. In the subsequent step, by adopting another previously reported synthetic approach, we obtained the alcohol (10) by addition of ethylene oxide to lithiated 1-ethynyladamantane using catalytic amounts of trimethylaluminum (TMA) to promote the reaction. To introduce the desired amino group, 4-(1'-adamantyl)-3-butyn-1-ol (10) was converted to the corresponding mesylate (11) using methanesulfonyl chloride/Et$_3$N, followed by the conversion to azide (12) using NaN$_3$ in DMF at 70° C. by implementing the synthetic procedure reported by Taylor et al (Taylor, E. Macor, J. E., Pont, J. Intramolecular Diels-Alder reactions of 1,2,4-triazines. A general synthesis of furo[2,3-b]pyridines, 2,3-dihydropyrano[2,3-b]pyridines, and pyrrolo[2,3-b]pyridines, *Tetrahedron*, 1987, 43, 5145). The azide was then reduced to the desired amino derivative (13).

Synthesis of 1-Ethynyladamantane (9). Potassium tert-butoxide (4.2 g, 37.9 mmol) was loaded in Schlenk flask inside an argon-filled glovebox. Using anhydrous techniques, the flask was charged with freshly distilled THF (20 mL), cooled to −10° C., after which (8) (4.1 g, 12.6 mmol) was added in a dropwise manner and the reaction mixture was stirred at room temperature under argon for 4d. The reaction was then quenched using water and the mixture was twice extracted using 20 mL of diethyl ether. The combined organic layers were washed with water and brine and then dried over anhydrous sodium sulfate. After filtration, the filtrate was vacuum-dried and the residue was flushed through a silica gel column using hexanes. The eluate was concentrated to afford white solid as the pure product (1.8 g, 91%). $^1$H NMR (500 MHz, CDCl$_3$, J=Hz): δ 2.08 (1H, s, CCH), 1.94 (3H, m, CH$_{ad}$), 1.87 (6H, m, CH$_{2ad}$), 1.67 (6H, m, CH$_{2ad}$). $^{13}$C NMR (125.8 MHz, CDCl$_3$): δ 93.1 (HCC), 66.6 (HCC), 42.7, 36.3, 29.4, 27.9 (C$_{ad}$). MS (GCEI, pos) for C$_{12}$H$_{16}$ (m/z): calcd 160.1252 (M). found 160.0990. 4-(1'-Adamantyl)-3-butyn-1-ol (10). To a solution of alkyne (9) (1.9 g, 18.2 mmol) in 12 mL of THF at −65° C. was added dropwise n-BuLi (8.7 mL of a 2.5 M solution in hexane, 21.9 mmol). After 2 h at −65° C., the flask was allowed to warm to −5° C. and trimethylaluminum (1.8 mL, 2 M solution in hexane, 3.64 mmol) was added dropwise. Following this, ethylene oxide was bubbled through the reaction mixture for 10 min. The reaction flask was maintained at room temperature for 2d, after which it was quenched by the addition of water (20 mL) and diethyl ether (10 mL). The mixture was transferred to a separatory funnel, the organic layer removed and the aqueous layer was extracted twice with 20 mL of diethyl ether. The combined organics were washed with brine and dried over anhydrous sodium sulfate, filtered and concentrated under reduced pressure. The residue was purified by silica gel chromatography eluting with diethyl ether-hexane to afford 1.83 g of alcohol (10) in 49% yield. $^1$H NMR (400 MHz, CDCl$_3$, J=Hz): δ 3.60 (2H, m, CH$_2$OH), 2.39 (2H, t, J 6.2, CH$_2$CH$_2$OH), 2.00 (1H, t, CH$_2$OH), 1.90 (3H, s, br, CH$_{ad}$), 1.80 (6H, m, CH$_{2ad}$), 1.63 (6H, m, CH$_{2ad}$). $^{13}$C NMR (100.6 MHz, CDCl$_3$): δ 91.4 (C$_{ad}$CC), 74.8 (C$_{ad}$CC), 61.3 (CH$_2$OH), 43.2, 36.4, 29.5, 28.0 (C$_{ad}$), 23.2 (CH$_2$CH$_2$OH). IR (KBr, cm$^{-1}$): v 3329 (br), 2910 (br), 2848 (s), 1450 (s), 1435 (sh), 1356 (w), 1344 (m), 1317 (w), 1259 (s), 1182 (w), 1099 (s), 1061 (sh), 1043 (s), 1018 (s), 976 (sh), 931 (w), 859 (w), 849 (w), 810 (s), 691 (w), 668 (w), 546 (w), 505 (w), 455 (w). HRMS (ESI, neg) for C$_{14}$H$_{21}$O (m/z): calcd 205.1592 (M+H). found 205.1848.

Synthesis of 4-(1'-Adamantyl)-3-butyn-1-mesylate (11). Methanesulfonylchloride (0.11 mL, 1.47 mmol) was added dropwise to a stirred solution of (10) (250 mg, 1.23 mmol) and triethylamine (0.2 mL, 1.47 mmol) in anhydrous diethyl ether (3 mL) at −15° C. under an argon atmosphere. After 3.5 h water (10 mL) and diethyl ether (10 mL) were added to the reaction mixture. The organic layer was separated, washed three times each with 20 mL of water and brine, then dried over anhydrous Na$_2$SO$_4$ and evaporated to yield (11) (300 mg, 87%) as a pale yellow oil. $^1$H NMR (400 MHz, CDCl$_3$, J=Hz): δ 4.15 (2H, t, J 7.0, CH$_2$OMs), 2.96 (3H, s, CH$_3$), 2.53 (2H, t, J 6.8, CH$_2$CH$_2$OMs), 1.85 (3H, m, CH$_{ad}$), 1.73 (6H, m, CH$_{2ad}$), 1.58 (6H, s, br, CH$_{2ad}$). $^{13}$C NMR (100.6 MHz, CDCl$_3$): δ 91.3 (C$_{ad}$CC), 72.8 (C$_{ad}$CC), 68.3 (CH$_2$OMs), 42.8 (C$_{ad}$), 37.4 (CH$_2$CH$_2$OMs), 36.2, 29.3, 27.8 (C$_{ad}$), 19.7 (CH$_3$). HRMS (GCEI, pos) for C$_{15}$H$_{22}$O$_3$S (m/z): calcd 282.1290 (M). found 282.1107; for C$_{14}$H$_{18}$ (m/z): calcd 186.1409 (M−HOSO$_2$Me). found 186.1231.

Synthesis of 1-(4'-Azido-1'-butynyl)adamantane (12). Sodium azide (212 mg, 2.65 mmol) was added to a solution of mesylate (11) (300 mg, 1.06 mmol) in dry DMF (3 mL) under argon. The mixture was stirred at 70° C. for 6.5 h. The reaction mixture was poured into water (20 mL) and extracted with diethyl ether (3×20 mL). The solution was then washed with brine, dried over anhydrous Na$_2$SO$_4$ and evaporated to yield (12) (240 mg, 98%) as a pale yellow liquid. $^1$H NMR (500 MHz, CDCl$_3$, J=Hz): δ 3.27 (2H, t, J 5.0, CH$_2$N$_3$), 2.42 (2H, t, J 7.5, CH$_2$CH$_2$N$_3$), 1.89 (3H, m, CH$_{ad}$), 1.79 (6H, m, CH$_{2ad}$), 1.63 (6H, m, CH$_{2ad}$). $^{13}$C NMR (125.8 MHz, CDCl$_3$): δ 91.5 (C$_{ad}$CC), 74.7 (C$_{ad}$CC), 50.3 (CH$_2$N$_3$), 42.9, 36.4, 29.4, 27.9 (C$_{ad}$), 20.0 (CH$_2$CH$_2$N$_3$). IR (KBr, cm$^{-1}$): v 2930 (sh), 2904 (s), 2850 (m), 2096 (s), 1452 (m), 1359 (w), 1345 (w), 1334 (w), 1297 (w), 1274 (w), 1248 (w), 1222 (sh), 1182 (w), 1102 (w), 1033 (w), 975 (w), 958 (w), 931 (w), 917 (w), 813 (w), 668 (w), 554 (w), 500 (w). HRMS (APCI, pos) for C$_{14}$H$_{21}$N$_3$ (m/z): calcd 231.1735 (M+2H)$^+$. found 231.2220.

Synthesis of 4-(1'-Adamantyl)-3-butyn-1-amine (13). Under an argon atmosphere and to a stirred solution of azide (12) (490 mg, 2.14 mmol) in tetrahydrofuran (THF) (10 mL) was added slowly a 2 M solution of lithium aluminum hydride in THF (0.89 mL 2.2 mmol) at 5° C. The mixture was slowly warmed to room temperature and stirred overnight. Upon completion, water was added dropwise to quench the excess LAH. The mixture was filtered through a pad of Celite and sodium sulfate, and the filtrate vacuum-dried to afford the yellow oil as a pure product (380 mg, 88%). $^1$H NMR (500 MHz, CDCl$_3$, J=Hz): δ 2.73 (2H, t, J 5.0, CH$_2$NH$_2$), 2.26 (2H, t, J 5.0, CH$_2$CH$_2$NH$_2$), 1.91 (3H, m, CH$_{ad}$), 1.81 (6H, m, CH$_{2ad}$), 1.64 (6H, m, CH$_{2ad}$). $^{13}$C NMR (125.8 MHz, CDCl$_3$): 590.8 (C$_{ad}$CC), 76.3 (C$_{ad}$CC), 43.3 (C$_{ad}$), 41.5

($CH_2NH_2$), 36.3, 29.7, 28.0 ($C_{ad}$), 23.9 ($CH_2CH_2NH_2$). HRMS (APCI, pos) for $C_{14}H_{22}N$ (m/z): calcd 204.1752 (M+H)$^+$. found 204.2294.

Synthesis of Trans-N-(3'-(1"-adamantyl)-2'-propyn-1'-yl)-3-(3'"pyridyl)acrylamide (4). Compound (4) was prepared and isolated by treating (13) (360 mg, 1.77 mmol) with trans-3-(3'-pyridyl)acrylic acid (317 mg, 2.13 mmol), triethylamine (0.73 mL, 58.31 mmol), and BOP (941 mg, 2.13 mmol) in dimethylforrnamide (7 mL) overnight to yield yellow solid (4) (390 mg, 66%). $^1$H NMR (500 MHz, CDCl$_3$, J=Hz): 8.74 (1H, m, H$_{arom}$), 8.56 (1H, d, J 5.0, H$_{arom}$), 7.79 (1H, d, J 5.0, H$_{arom}$), 7.61 (1H, d, J$_{trans}$=15.0, CH=CH), 7.30 (1H, m, H$_{arom}$), 6.45 (1H, d, J$_{trans}$=15.0, CH=CH), 5.90 (1H, s, br, O=CNH), 3.48 (2H, m, CH$_2$NH), 2.43 (2H, t, J 15.0, CH$_2$CH$_2$NH), 1.93 (3H, m, CH$_{ad}$), 1.82 (6H, m, CH$_{2ad}$), 1.66 (6H, s, br, CH$_{2ad}$). $^{13}$C NMR (100.6 MHz, CDCl$_3$): δ 165.0 (C=O), 150.4, 149.2, 137.4, 134.4, 130.7, 123.7, 122.9 (C$_{arom}$+CH=CH), 91.2 (C$_{ad}$CC), 75.4 (C$_{ad}$CC), 43.3 (C$_{ad}$, 38.8 (CH$_2$NH), 36.3, 29.5, 28.0 (C$_{ad}$), 197 (CH$_2$CH$_2$NH$_2$). HRMS (APCI, pos) for $C_{22}H_{27}N_2O$ (m/z): calcd 335.2123 (M+H)$^+$. found 335.2581.

Example 5

1-(4'-(Trans-3"-(3'"pyridyl)acrylamido)butyl)-1,7-dicarba-closo-dodecaborane (6)

Figure 5:
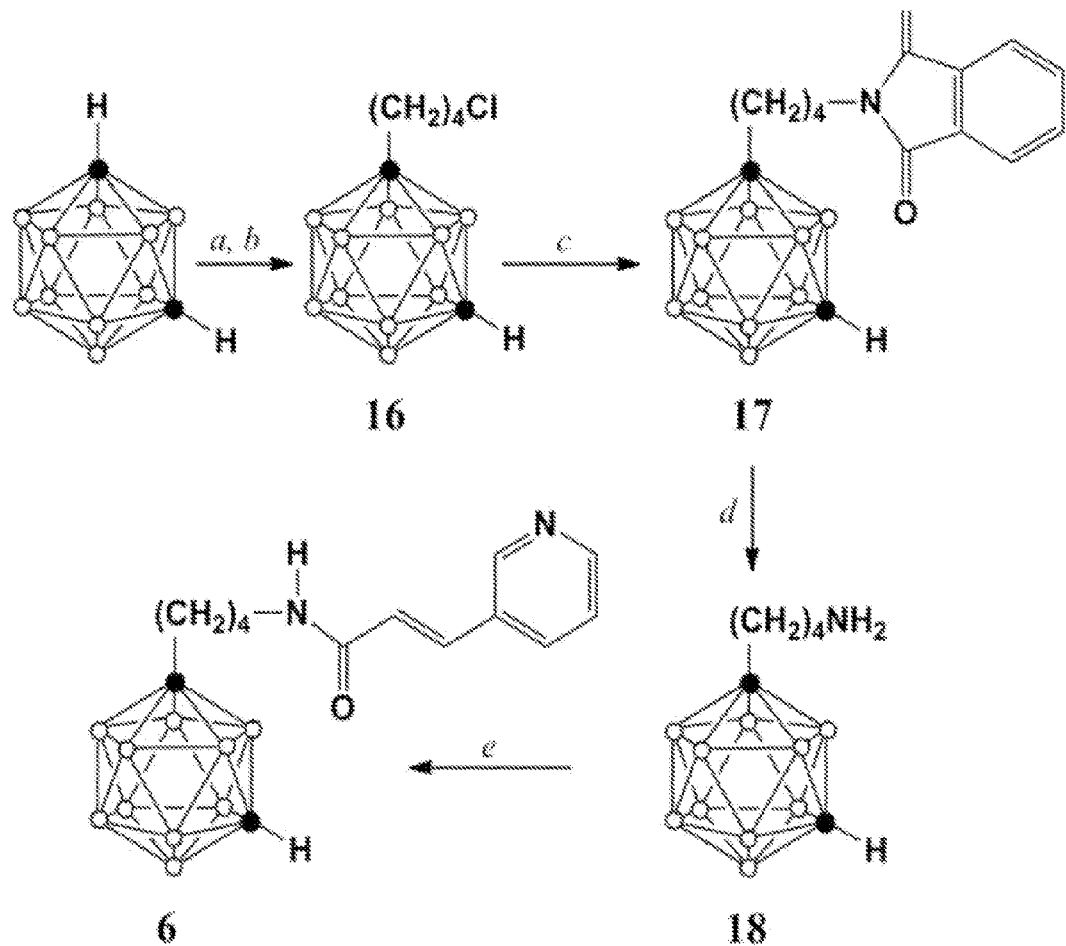
FIG. 5 shows a synthetic route to compound (6). Reagents and conditions: a) $^n$BuLi, THF, 4 h, rt; b) Cl(CH$_2$)$_4$I, overnight rt; c) KN(CO)$_2$C$_6$H$_4$, DMF, reflux overnight; d) N$_2$H$_4$, EtOH, 4.5 h reflux, e) DMF, BOP, Et$_3$N, C$_5$NH$_4$(CH$_2$)COOH, overnight rt.

Compound (6) was prepared in four synthetic steps as depicted in FIG. 5.

1-(chlorobutyl)-1,7-dicarba-closo-dodecaborane (16). To 1.08 g (7.50 mmol) of m-carborane in 20 mL of freshly distilled tetrahydrofuran at 0° C. was added 3 mL (7.50 mmol) of 2.5 M n-butyllithium in hexane. The mixture was stirred for 4 h allowed to slowly warm to room temperature. The mixture was cooled to −60° C. and 1-chloro-4-iodobutane (0.92 mL, 7.50 mmol) was added dropwise and the resulting solution was allowed to slowly warm to room temperature and stirred overnight. To quench the reaction, an aqueous solution of ammonium chloride was added and the mixture was extracted three times with 20 mL of diethyl ether; the organic phase was washed with brine (5 mL) and then dried over anhydrous sodium sulfate. The solvent was removed in vacuo and the resulting crude residue was purified by silica gel column chromatography using hexanes to afford a m-[B$_{10}$C$_2$H$_{11}$](CH$_2$)$_4$Cl (16) as a colorless oil. The yield was 0.67 g (41%). The di-substituted product, m-[B$_{10}$C$_2$H$_{10}$((CH$_2$)$_4$Cl)$_2$ (16a), was also isolated (0.75 g, 33%). (16): $^1$H NMR (300 MHz, CD$_2$Cl$_2$, J=Hz): 3.51 (2H, t, J 6.5 Hz, CH$_2$Cl), 3.00 (1H, s, br, C$_{carborane}$—H), 1.99 (2H, m, C$_{carborane}$—CH$_2$), 1.69 (2H, m, CH$_2$), 1.53 (2H, m, CH$_2$), 3.3-1.2 (10H, BH). $^{13}$C NMR (75.5 MHz, CD$_2$Cl$_2$): δ 76.6 (C$_{carborane}$—CH$_2$), 55.6 (H—C$_{carborane}$), 44.8 (CH$_2$Cl), 36.5 (C$_{carborane}$—CH$_2$), 32.3, 27.7 (CH$_2$). $^{11}$B NMR (96.3 MHz, CD$_2$Cl$_2$, J=Hz): δ −4.4 (1B, d, J 161), −11.2 (5B, d, J 154), −13.8 (2B, d, J 160), −15.5 (2B, d, J 174). HRMS (APCI, neg) for $C_6H_{18}ClB_{10}$ (m/z): calcd 234.2076 (M−H)$^-$. found 234.2323. (19a): HRMS (ESI, neg) for $C_{10}H_{27}Cl_3B_{10}$ (m/z): calcd 360.2091 (M+Cl). found 360.2101.

1-(Phthalimido-N-butyl)-1,7-dicarba-closo-dodecaborane (17). A sample of 1.55 g (6.56 mmol) of (16) was dissolved in 6 mL of dimethylformamide. The reaction mixture was cooled to 0° C. and potassium phthalimide (1.27 g, 6.89 mmol) in 20 mL dimethylformamide was added dropwise via syringe. The mixture was allowed to warm to room temperature while stirring for 30 min and then refluxed overnight, after which it was quenched by the addition of deionized water (20 mL) and ethyl acetate (20 mL). The organic layer was separated and the aqueous layer was washed twice with ethyl acetate. The combined organic phases were washed with brine and dried over anhydrous sodium sulfate. After the solvents were removed in vacuo, the residue was purified by silica gel column chromatography with hexane followed by an increasing ratio of dichloromethane as eluent. The hexane/dichloromethane eluate was concentrated under vacuum to afford the product as a white solid (1.44 g, 63%). $^1$H NMR (300 MHz, CD$_2$Cl$_2$, J=Hz): δ 7.84-7.70 (4H, m, H$_{arom}$), 3.62 (2H, t, J 7.1, CH$_2$N), 3.00 (1H, s, br, C$_{carborane}$—H), 2.00 (2H, m, C$_{carborane}$—CH$_2$), 1.59 (2H, m, CH$_2$), 1.42 (2H, m, CH$_2$), 3.4-1.1 (10H, BH). $^{13}$C NMR (75.5 MHz, CD$_2$Cl$_2$): δ 168.5 (C=O), 134.3, 132.5, 123.3 (C$_{arom}$), 76.6 (C$_{carborane}$—CH$_2$), 55.5 (H—C$_{carborane}$), 37.5 (CH$_2$N), 36.6 (C$_{carborane}$—CH$_2$), 28.3, 27.5 (CH$_2$). $^{11}$B NMR (96.3 MHz, CD$_2$Cl$_2$, J=Hz): δ −4.3 (1B, d, J 161), −11.2 (5B, d, J 154), −13.9 (2B, d, J 160), −15.5 (2B, d, J 172). HRMS (APCI, neg) for $C_{14}H_{23}NO_2B_{10}$ (m/z): calcd 345.2739 (M)$^-$. found 345.2737.

1-(Aminobutyl)-1,7-dicarba-closo-dodecaborane (18). Compound (17) (1.44 g, 4.15 mmol) and hydrazine hydrate (1.4 mL, 41.5 mmol) in ethanol (30 mL) were heated under reflux for 4 h, after which the reaction mixture was cooled to room temperature and then to 0° C. The precipitate of phthalhydrazide was filtered and washed with a cold ethanol. The filtrate concentration under vacuum induced precipitation of a further amount of phthalhydrazide. The solution was filtered from insoluble material, cooled, and filtered again. Removal of the solvent left a residue which was dissolved in dichloromethane (10 mL) and filtered. The filtrate was evaporated under reduced pressure and redissolved in ethanol (3 mL). On cooling, a white precipitate formed. Filtration and removal of the solvent under reduced pressure left a thick oil (0.70 g, 77%). $^1$H NMR (500 MHz, CD$_2$Cl$_2$, J=Hz): δ 3.00 (1H, 5, br, C$_{carborane}$—H), 2.63 (2H, t, J 6.8, CH$_2$NH$_2$), 1.95 (2H, m, C$_{carborane}$—CH$_2$), 1.70 (2H, s, br, NH$_2$), 1.36 (4H, m, CH2), 3.9-0.7 (10H, BH). $^{13}$C NMR (125.8 MHz, CD$_2$Cl$_2$): δ 77.1 (C$_{carborane}$—CH$_2$), 55.5 (H—C$_{carborme}$), 42.0 (CH$_2$NH$_2$), 37.2 (C$_{carborane}$—CH$_2$), 33.4, 27.7 (CH$_2$). $^{11}$B NMR (96.3 MHz, CD$_2$Cl$_2$, J=Hz): δ −4.2 (1B, d, J 160), −11.1 (5B, d, J 154), −13.8 (2B, d, J 159), −15.4 (2B, d, J 171). HRMS (APCI, pos) for $C_6H_{22}NB_{10}$ (m/z): calcd 216.2759 (M+H)$^+$. found 216.2559.

1-(4'-(Trans-3"-(3'"-pyridyl)acrylamido)butyl)-1,7-dicarba-closo-dodecaborane (6). Compound (17) (70 mg, 0.32 mmol) and trans-3-(3'-pyridyl)acrylic acid (57 mg, 0.39 mmol) were dissolved in DMF (12 mL) and triethylamine (0.13 mL) was added, followed by BOP (170 mg, 0.39 mmol). The reaction mixture was allowed to stir at room temperature overnight, after which it was quenched by the addition of water (20 mL) and ethyl acetate (20 mL). The biphasic mixture was transferred to a separatory funnel; the organic layer was removed and the aqueous layer was extracted with twice with 20 mL of ethyl acetate. The organic fractions were combined and washed with 20 mL of water and 3 mL of brine, dried over anhydrous Na$_2$SO$_4$ and the solvent removed under vacuum. The residue was purified by silica gel chromatography (dichloromethane/methanol) to afford a yellow oil (40 mg, 36%). $^1$H NMR (300 MHz, CD$_3$CN, J=Hz): δ 8.70 (1H, d, J 1.8, H$_{arom}$), 8.51 (1H, dd, $^3$J 4.8, $^4$J 1.5, H$_{arom}$), 7.89 (1H, dt, J$_d$ 7.8, J$_t$ 1.8, H$_{arom}$), 7.47 (1H, d, J$_{trans}$=15.9, CH=CH), 7.34 (1H, m, H$_{arom}$), 6.72 (1H, s, br, O=CNH), 6.61 (1H, d, J$_{trans}$ 15.9, CH=CH), 3.30 (1H, 5, br, C$_{carborane}$—H), 3.21 (2H, m, CH$_2$NH), 1.97 (2H, m, C$_{carorane}$—CH$^2$), 1.40 (4H, m, CH$_2$), 3.7-1.0 (10H, BH). $^{13}$C NMR (75.5 MHz, CD$_3$OD): δ 167.7 (C=O), 150.7, 149.7, 137.5, 136.3, 132.9, 125.5, 124.7 (C$_{arom}$+CH=CH), 77.6 (C$_{carborane}$—CH$_2$), 56.9 (H—C$_{carborane}$), 40.0 (CH$_2$NH), 37.7 (C$_{carborane}$—CH$_2$), 29.9, 28.5 ($CH_2$). $^{11}$B NMR (96.3 MHz, $CD_3OD$, J=Hz): δ −3.7 (1B, d, J 159), −10.4 (5B, d, J 154), −13.0 (2B, d, J 159), −14.6 (2B, d, J 169). HRMS (TIS, pos) for $C_{14}H_{27}N_2OB_{10}$ (m/z): calcd 347.3134 $(M+H)^+$. found 347.3040.

Example 6

1-(4'-(Trans-3''-(3'''-pyridyl)acrylamido)butyl)-1,12-dicarba-closo-dodecaborane (7)

Figure 6:
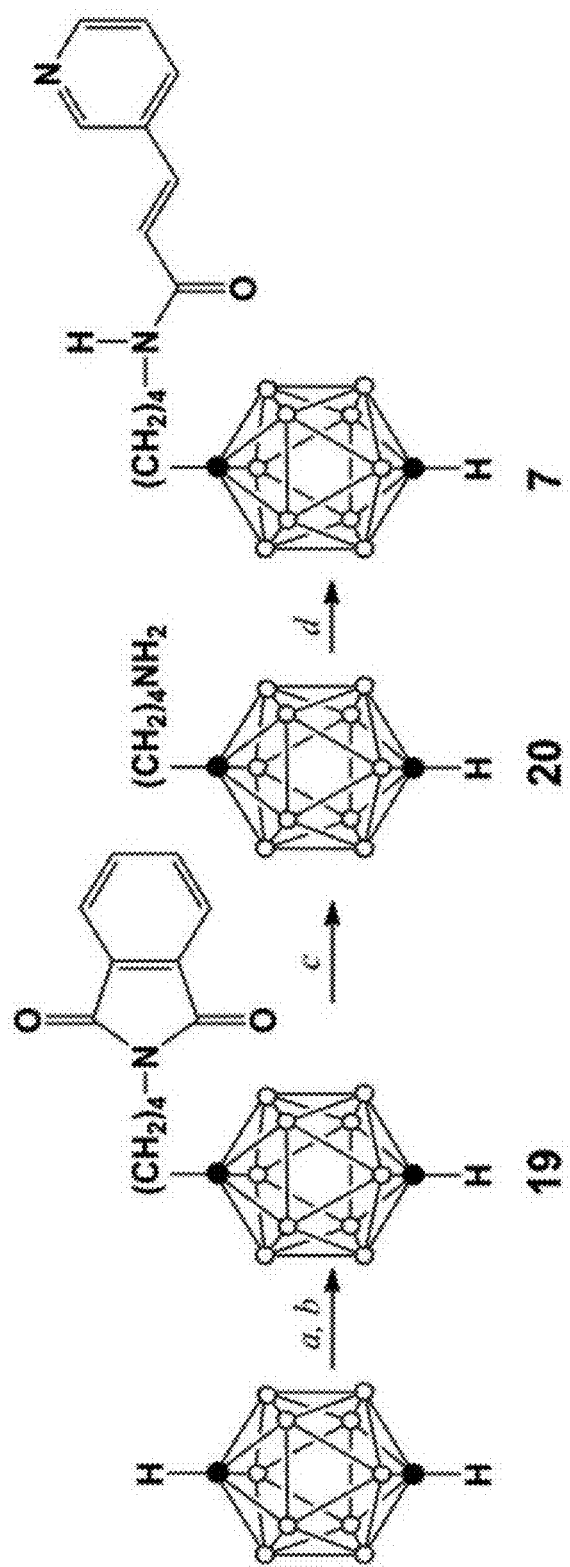
FIG. 6 shows a synthetic route to compound (7). Reagents and conditions: a) $^n$BuLi, THF, 5 h rt; b) Br(CH$_2$)$_4$N(CO)$_2$C$_6$H$_4$, overnight rt; c) 10 N$_2$H$_4$, EtOH, 4 h reflux; d) DMF, BOP, Et$_3$N, C$_5$NH$_4$(CH)$_2$COOH, overnight rt.

Synthesis of the p-carborane derivative (7) is depicted in FIG. 6. The synthesis was adapted from the synthetic strategy previously described for the meta-carborane analogue (6), except that (phthalimido-N-butyl)-p-carborane (7) could be prepared directly from p-carborane in a reasonable yield when accounted for the formation of the corresponding disubstituted product.

1-(Phthalimido-N-butyl)-1,12-dicarba-doso-dodecaborane (19). To 96 mg (0.67 mmol) of p-carborane in 12 mL of freshly distilled tetrahydrofuran at 0° C. was added 0.27 mL (0.67 mmol) of 2.5 M n-butyllithium. The mixture was stirred for 1 h in an ice bath, allowed to warm to room temperature and stirred for 4 h. The mixture was cooled to −60° C. and N-(4-bromobutyl)phthalimide (188 mg, 0.67 mmol) was added. The resulting solution was allowed to slowly warm to room temperature and stirred overnight. The reaction was quenched using an aqueous solution of ammonium chloride and the mixture was extracted three times with 20 mL of diethyl ether and the organic layer was dried over anhydrous sodium sulfate. The solvent was removed in vacuo to result in a crude residue that was purified by silica gel column chromatography using a mixture of hexane/dichloromethane to afford a white powder of p-$[B_{10}C2H_{11}](CH_2)_4N(CO)_2C_6H_4$ (19). The yield was 90 mg (39%). The disubstituted product, p-$[B_{10}C_2H_{10}]$ $\{(CH_2)_4N(CO)_2C_6H_4\}_2$, was also isolated (100 mg, 27%). $^1$H NMR (300 MHz, $CDCl_3$, J=Hz): δ 7.83-7.67 (4H, m, $H_{arom}$), 3.55 (2H, t, J 7.4, $CH_2N$), 2.60 (1H, s, br, $C_{carborane}$—H) 1.63 (2H, m, $C_{carborane}$—$CH_2$), 1.46 (2H, m, $CH_2$), 1.19 (2H, m, CH2), 3.2-1.1 (10H, BH). $^{13}$C NMR (125.8 MHz, $CDCl_3$): δ 168.3 (C=O), 133.9, 132.0, 123.2 ($C_{arom}$), 84.2 ($C_{carborane}$—$CH_2$), 58.1 (H—$C_{carborane}$), 38.2 ($CH_2N$), 37.3 ($C_{carborane}$—$CH_2$), 28.0, 26.5 ($CH_2$). $^{11}$B NMR (96.3 MHz, $CDCl_3$, J=Hz): δ −12.8 (5B, d, J 170), −15.3 (5B, d, J 172). HRMS (APCl, neg) for $C_{14}H_{23}NO_2B_{10}$ (m/z): calcd 345.2739 $(M)^-$. found 345.2712.

1-(Aminobutyl)-1,12-dicarba-closo-dodecaborane (20). Compound (19) (208 mg, 0.60 mmol) and hydrazine hydrate (0.2 mL, 6.00 mmol) in ethanol (20 mL) were heated at reflux for 4 h. A white precipitate of phthalhydrazide began to form after ca. 2 h. The reaction mixture was cooled to room temperature and then to 0° C. for 2 h. The solid was filtered and washed with a cold ethanol and then dried (150 mg). Removal of the solvent under reduced pressure left a thick oil. The sample was dissolved in 5 mL of ethanol and cooled to 4° C. overnight, resulting in the precipitation of additional phthalhydrazide, which was removed by filtration. The filtrate was evaporated under reduced pressure and redissolved in ethanol (3 mL) to which was added diethyl ether (5 mL). On cooling, white powder was deposited. Recrystallization from ethanol, ethyl ether and hexane gave the 1-(aminobutyl)-1,12-dicarba-closo-dodecaborane (20). The yield was 100 mg (76%). $^1$H NMR (300 MHz, $CD_3OD$, J=Hz): δ 3.10 (1H, s, br, $C_{carborane}$—F), 2.57 (2H, t, J 7.1, $CH_2NH_2$), 1.65 (2H, m, $C_{carborane}$—$CH_2$), 1.27 (4H, m, $CH_2$), 3.2-1.1 (10H, BH). $^{13}$C NMR (75.5 MHz, $CD_3OD$): δ 85.8 ($C_{carbonane}CH_2$), 59.9 (H—$C_{carborane}$), 41.8 ($CH_2NH_2$), 39.9 ($C_{carborane}$—$CH_2$), 30.8, 27.9 ($CH_2$). $^{11}$B NMR (96.3 MHz, $CD_3OD$, J=Hz): δ −12.2 (5B, d, J 170), −14.6 (5B, d, J 173).

1-(4'-(Trans-3''-(3'''-pyridyl)actylamido)butyl)-1,12-dicarba-closo-dodecaborane (7). Compound (20) (100 mg, 0.46 mmol) and trans-3-(3'-pyridyl)acrylic acid (82 mg, 0.55 mmol) were dissolved in DMF (12 mL) and triethylamine (0.2 mL) was added, followed by BOP (243 mg, 0.55 mmol). The reaction mixture was allowed to stir at room temperature overnight, after which it was quenched by the addition of water (20 mL) and ethyl acetate (20 mL). The biphasic mixture was transferred to a separatory funnel; the organic layer was removed and the aqueous layer was extracted twice with 20 mL of ethyl acetate. The organic fractions were combined and washed with 20 mL of water and 3 mL of brine and then dried over anhydrous $Na_2SO_4$. The solvent was removed under vacuum and the residue was purified by silica gel chromatography using dichloromethane/methanol to afford a yellow oil (30 mg, 19%). $^1$H NMR (500 MHz, $CD_3CN$, J=Hz): δ 8.70 (1H, d, J 2.0, $H_{arom}$), 8.51 (1H, dd, $^3$J 4.5, $^4$J 1.5, $H_{arom}$), 7.90 (1H, dt, $J_d$ 8.0, $J_t$ 1.8, $H_{arom}$), 7.46 (1H, d, $J_{trans}$ 16.0, CH=CH), 7.35 (1H, m, $H_{arom}$), 6.60 (1H, br, O=CNH), 6.59 (1H, d, $J_{trans}$ 16.0, CH=CH), 3.15 (2H, m, $CH_2NH$), 3.00 (1H, s, br, $C_{carborane}$—H), 1.66 (2H, m, $C_{carborane}$—$CH_2$), 1.31 (2H, m, $CH_2$), 1.18 (2H, m, $CH_2$), 2.8-0.8 (10H, BH). $^{13}$C NMR (125.8 MHz, $CD_3CN$): δ 165.8 (C=O), 151.2, 150.3, 136.7, 134.9, 131.9, 124.8, 124.7 ($C_{arom}$+CH=CH), 85.2 ($C_{carborane}$—$CH_2$), 59.7 (H—$C_{carborane}$), 39.5 ($CH_2NH$), 39.1 ($C_{carborane}$—$CH_2$), 29.6, 27.5 ($CH_2$). $^{11}$B NMR (96.3 MHz, $CD_3CN$, J=Hz): δ −12.0 (5B, d, J 168), −14.5 (5B, d, J 169). HRMS (APCl, pos) for $C_{14}H_{27}N_2OB_{10}$ (m/z): calcd 347.3134 $(M+H)^+$. found 347.3443.

Example 7

Synthetic Route Involving Carboxylic Acid Coupling

Two overall synthetic routes can be used to produce compound (5). Derivatives of o-carborane were produced by direct substitution of a carbon atom on o-carborane or by inserting an alkyne into decaborane to form the closo icosahedron. A strong base such as n-butyllithium can extract a weakly acidic proton of one (or both) carbon atoms in a carborane. The resulting anion reacts with electrophile, and was reacted with 1-bromo-4-chlorobutane. The resulting chloride was converted to a protected amine using di-tert-butyl dicarbonate. Subsequent deprotection of the amine was afforded by treatment with 4M HCl in dioxane. Alternatively, (5) can be produced using decarborane as the starting material. Reaction with a Lewis acid such as dihydrogen sulfide or acetonitrile gives $B_{10}H_{12}L_2$ which will react with a substituted alkyne to form the corresponding ortho carborane. This reaction inserts the carbon-carbon triple bond into the open face of $B_{10}H_{12}L_2$, forming the closo cluster. N-(5-hexynyl) phthalimide was used to achieve this reaction. The phthalimide was subsequently reduced by a reducing agent. Here the phthalimide was reduced using sodium borohydride, followed by refluxing in aqueous HCl.

Figure 7:
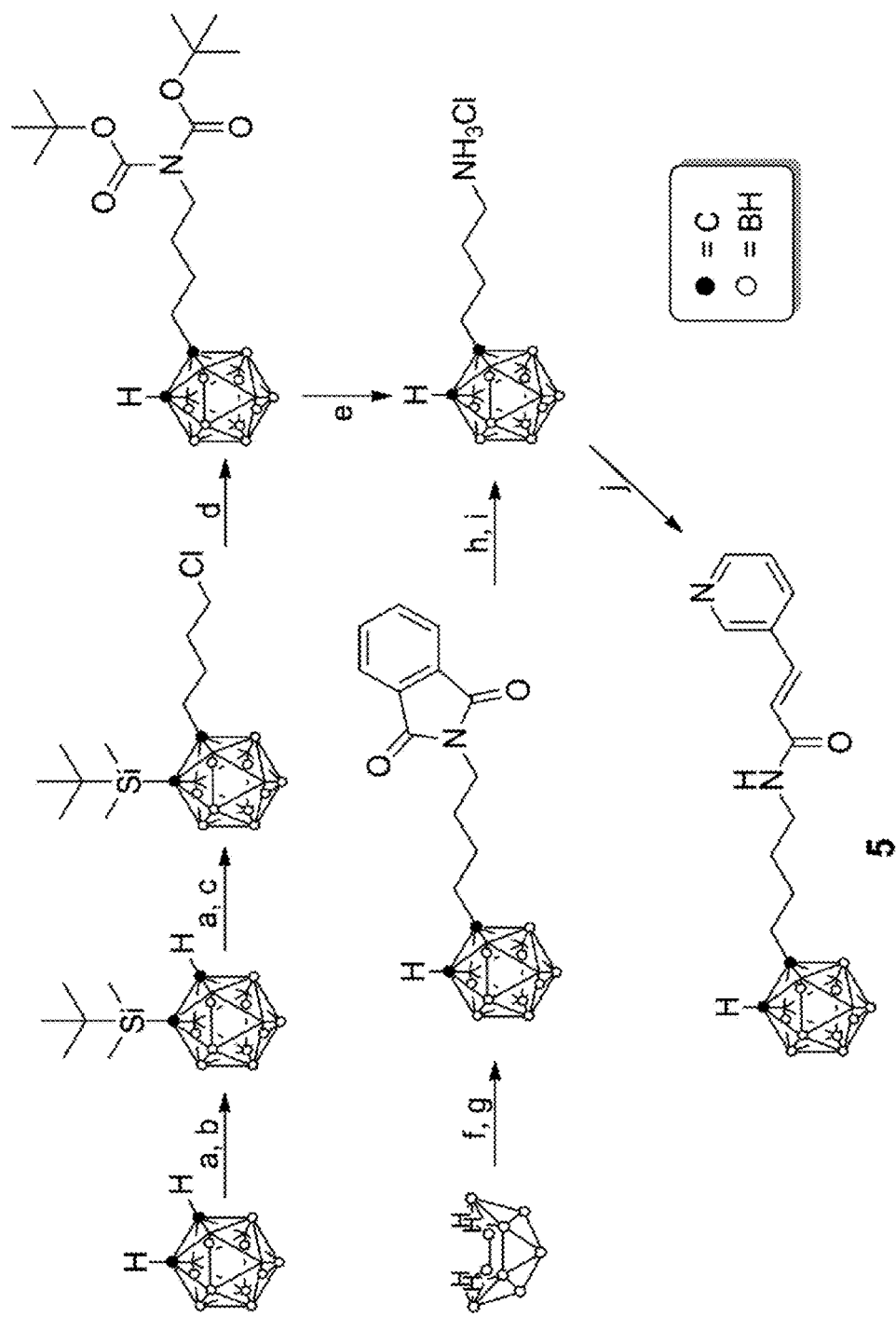
FIG. 7 shows two synthetic routes to compound (5). Reagents and conditions: a) $^n$BuLi, −78° C., 4 h; b) t-BuMe$_2$SiCl, −78° C., 1 h, rt; d) Cl(CH$_2$)$_4$Br, rt, 12 h; d) 5% LiI, Cs$_2$CO$_3$, NHBoc$_2$, 2-butanone, 2 days, reflux; e) 4M HCl in dioxane, rt, 3.5 h; f) Et$_2$S, toluene, 4 h reflux; g) HC$_2$(CH$_2$)$_4$N(CO)$_2$C$_6$H$_4$, 12 h reflux; h) NaBH$_4$, 6:1 2-propanol/H$_2$O, rt, 12 h; i) HCl$_{conc}$, reflux, 12 h, j) DMF, BOP, Et$_3$N, C$_5$H$_4$(CH$_2$)COOH, rt, 14 h.

Finally, for both synthetic routes, the final product (5) was prepared by coupling the amine with trans-3-(3'-pyridyl) acrylic acid using Castro's reagent (BOP) as the coupling agent. The overall scheme is shown in FIG. 7.

Example 8

Synthetic Route Involving Acyl Chloride Coupling 1-(4-Azidobutyl)-1,7-dicarbadodecaborane. In a 100 mL round bottom flask, 1-(4-Chlorobutyl)-1,7-dicarbadodecaborane. (1.50 g, 6.39 mmol) was dissolved in DMF (30 mL). Sodium azide (1.25 g, 19.17 mmol) and catalytic amount of NaI (0.095 g, 0.64 mmol) was added to the reaction mixture. The reaction mixture was covered with foil and refluxed overnight at 64° C. The solvent was evaporated and the crude product was redissolved in DCM (10 mL) and washed with deionized water (3×5 mL). The organic phase was dried over anhydrous sodium sulfate and solvent was removed under reduced pressure to afford m-[$B_{10}C_2H_{10}$]($CH_2$)$_4N_3$ as a colorless oil. Yield: 1.07 g (66.6%). $^1$H NMR (400 MHz, $CDCl_3$, δ=ppm, J=Hz): δ=3.26 (t, 2H, J 6.3), 2.91 (s, 1H), 1.95 (t, 2H, J 8.8), 1.48 (m, 4H), 3.33-1.41 (10H, BH). $^{13}$C NMR (100 MHz, $CDCl_3$): δ=76.25, 55.24, 51.30, 36.78, 28.79, 27.47 ppm. HRMS (GC/APCl, neg, (m/z)): calcd. for $C_6H_{19}B_{10}N_3$ [M-$N_2$]$^-$ 213.35. found: 212.23.

1-(4-Aminobutyl)-1,7-dicarbadodecaborane. In a 100 mL round bottom flask, 1-(4-Azidobutyl)-1,7-dicarbadodecaborane (1.50 g, 6.22 mmol) was dissolved in anhydrous methanol (20 mL). Catalytic amount of Pd/C (0.662 g, 0.62 mmol) was added to the reaction mixture and a balloon was used to pump hydrogen into the reaction vessel. The reaction vessel was purged every 2 hrs for 8 hrs, to expel any $N_2$ gas that was produced as the byproduct and the reaction was allowed to stir overnight at room temperature. The solvent was evaporated and the crude product was redissolved in DCM (10 mL) and washed with deionized water (10 mL). The organic layer was collected and washed using brine (10 mL) and the crude product was extracted with dichloromethane (3×10 mL). The organic phase was collected and dried over anhydrous sodium sulfate and solvent was removed under reduced pressure and crude product was purified by silica gel column chromatography using 100% DCM, 7% MeOH/DCM, 50% MeOH/DCM, and 100% MeOH respectively as eluents, to afford m-[$B_{10}C_2H_{10}$]($CH_2$)$_4NH_2$) as a colorless oil. Yield: 0.807 g (60.2%).

Figure 8:
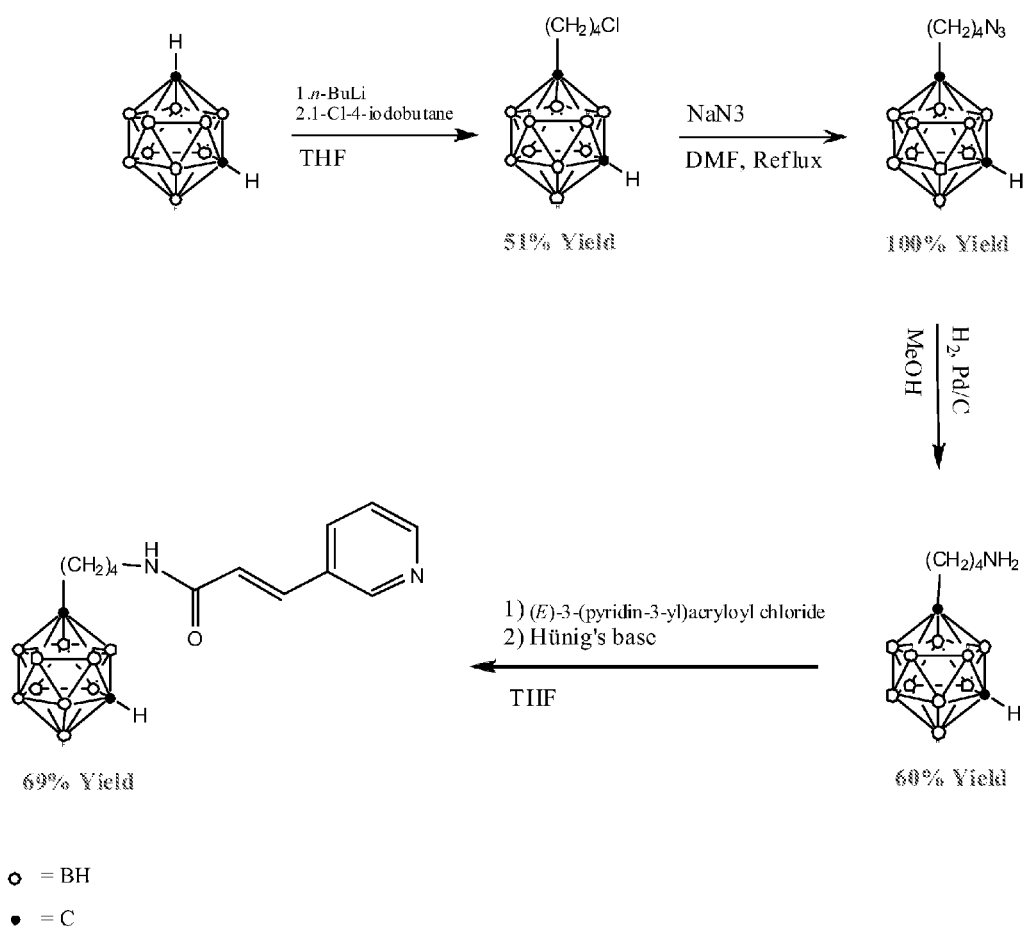
FIG. 8 shows an alternate synthetic route. Reagents and conditions: a) $^n$BuLi, THF, 4 h rt; b) Cl(CH$_2$)$_4$I, overnight rt; c) KN(CO)$_2$C$_6$H$_4$, DMF, reflux, overnight; d) N$_2$H$_4$, EtOH, 4.5 h reflux; e) DMF, BOP, Et$_3$N, C$_5$NH$_4$(CH)$_2$COOH, overnight rt.

1-(4'-(Trans-3"-(3'"-pyridyl)acrylamido)butyl)-1,7-dicarbadodecaborane. In a 250 mL 2-neck round bottom flask, trans-3-(3'-pyridyl)acrylic acid (0.510 g, 3.42 mmol) was suspended in anhydrous THF (20 mL) and DMF (1 mol %) was added as a catalyst. The solution was cooled to 0° C., while stirring, and thionyl chloride (0.814 g, 0.5 mL, 6.84 mmol) was added drop wise and the reaction mixture was allowed to reach ambient temperature while stirring overnight. The following day, the vessel was evacuated under reduced pressure to remove solvent and any gaseous byproducts. The crude product was redissolved in anhydrous THF (15 mL) and cooled to 0° C. 1-(4-Aminobutyl)-1,7-dicarbadodecaborane. (0.670 g, 3.11 mmol) was dissolved in anhydrous THF (5 mL) and Hünig's Base (1.860 g, 2.50 mL, 14.36 mmol) and added drop wise to the reaction vessel. The resulting solution was allowed to stir overnight while slowly reaching ambient temperature. The crude product was redissolved in DCM (10 mL) and washed with saturated solution of sodium bicarbonate (20 mL). The organic layer was collected and washed using brine (10 mL) and the crude product was extracted with dichloromethane (3×10 mL). The organic phase was collected and dried over anhydrous sodium sulfate and solvent was removed under reduced pressure and crude product was purified by silica gel column chromatography using a MeOH/$CHCl_3$ gradient, to afford 1-(4'-(Trans-3"-(3'"-pyridyl)acrylamido)butyl)-1,7-dicarbadodecaborane as a brown solid. Yield: 0.744 g (69%). For an overall schematic see FIG. 8.

Example 9

Scratch Test Assay

Figure 9:
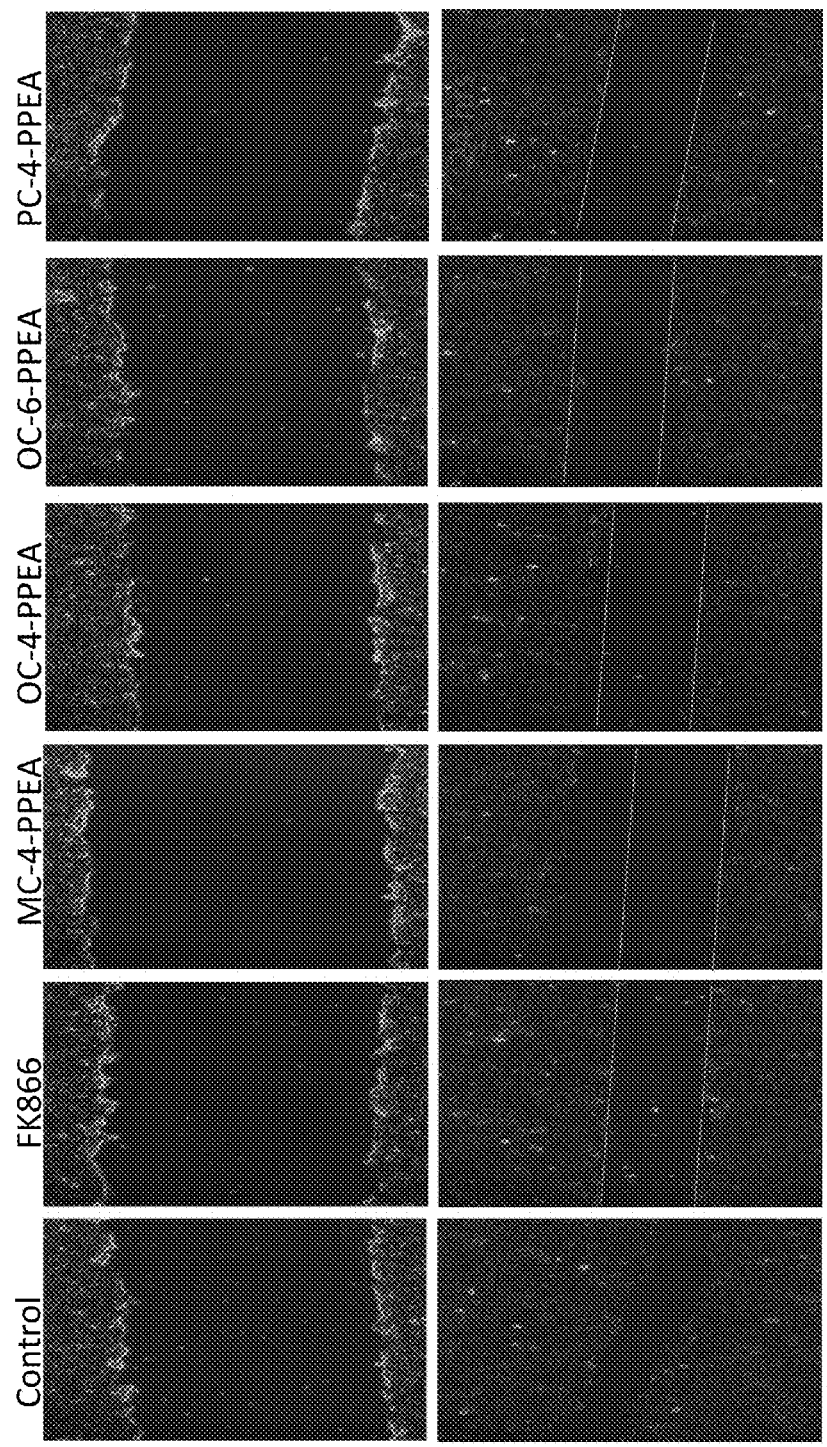
FIG. 9 shows the results of scratch test assays against DLD1 at 0 h and at 24 h.
Figure 10:
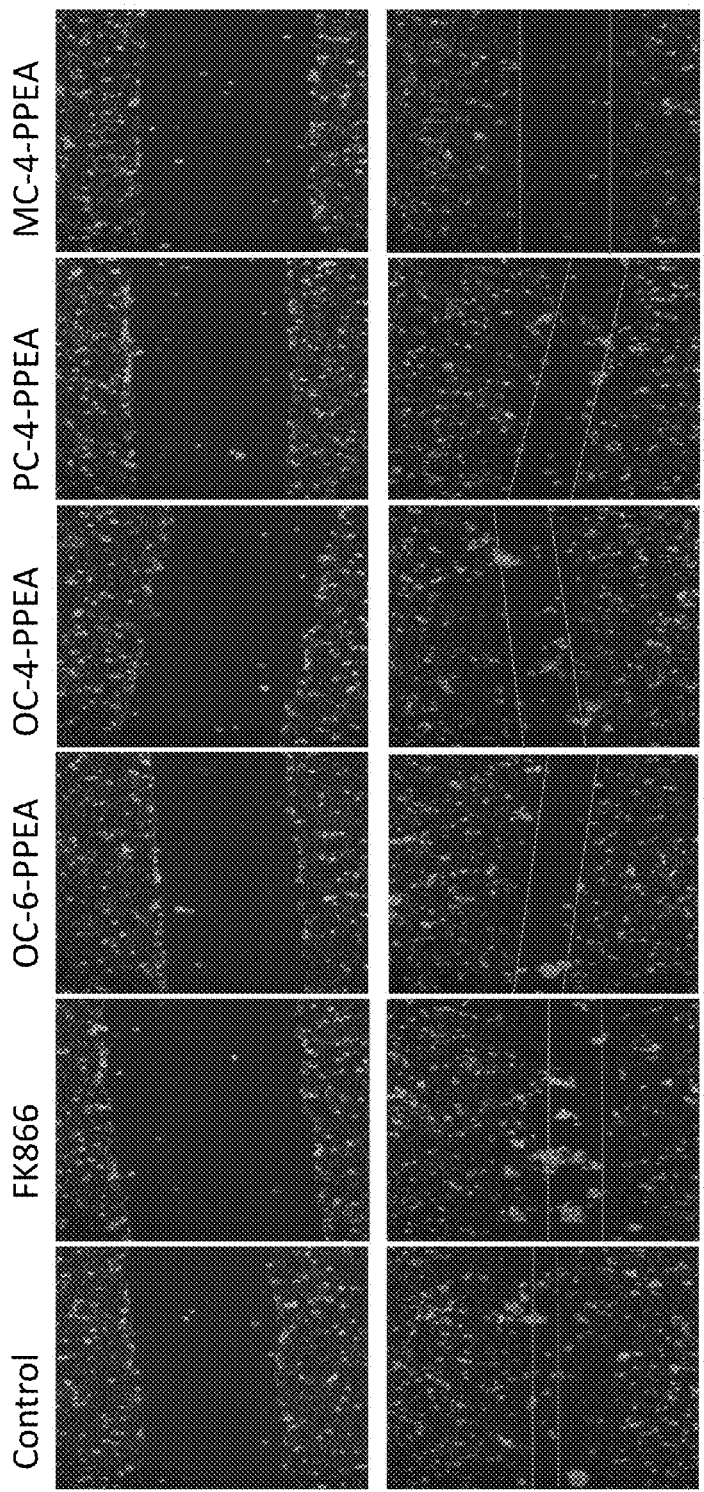
FIG. 10 shows the results of scratch test assays against A549 at 0 h and at 24 h.
Figure 11:
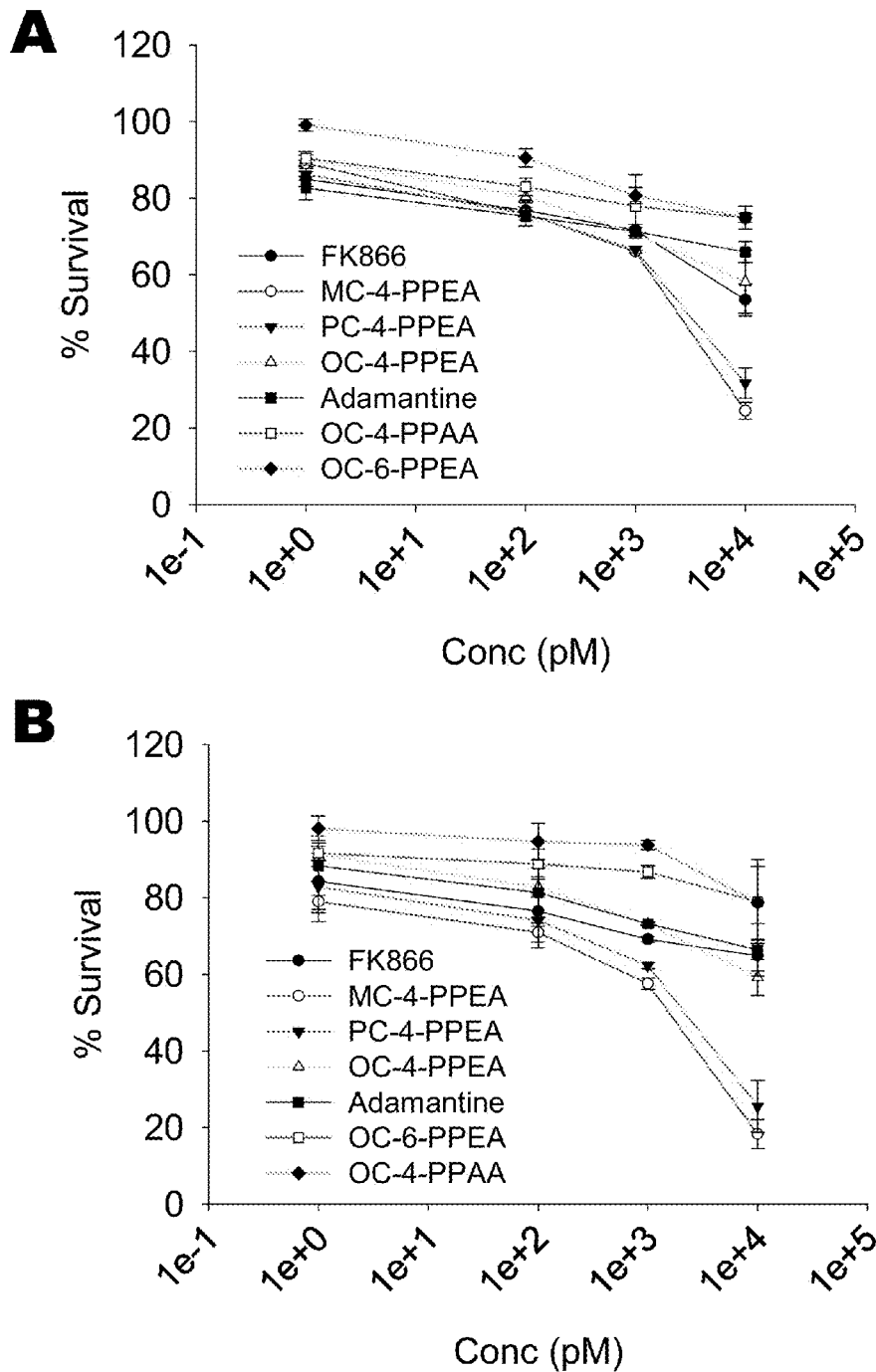
FIG. 11 (A)-(D) show results for MTT assays. (A) shows results of a PC3 MTT assay; (B) shows results of a T47D MTT assay; (C) shows results of a U87 MTT assay; and (D) shows a D1D1 MTT assay.
Figure 11:
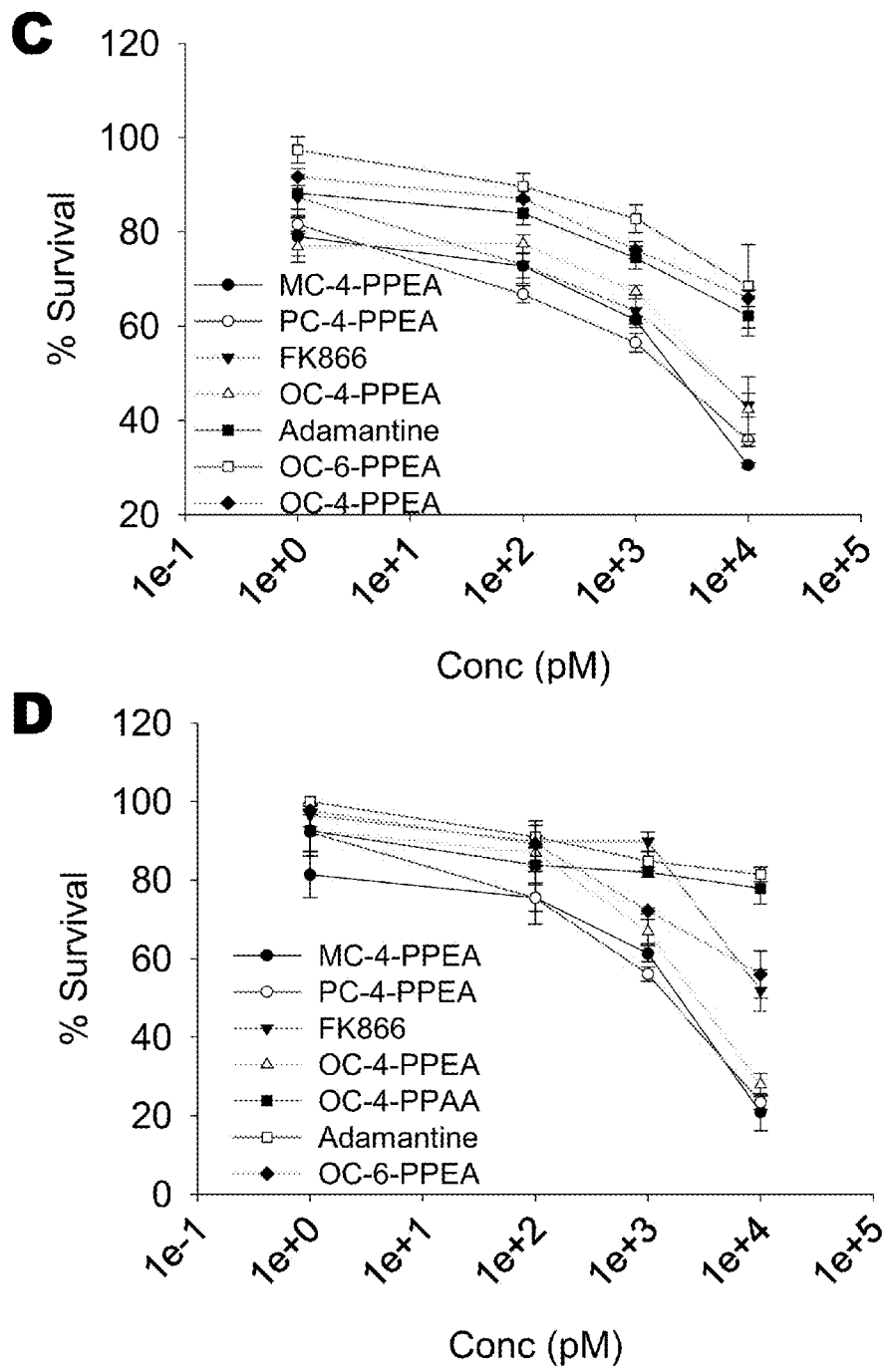
Figure 12:
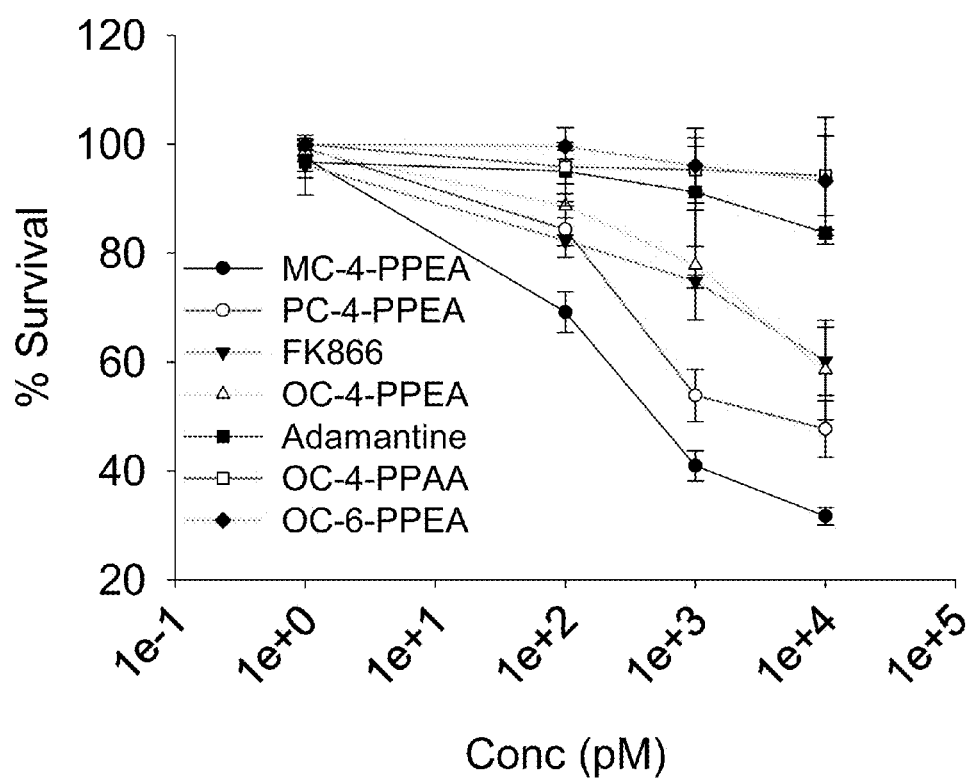
FIG. 12 shows results of a A549 MTT assay.
Figure 13:
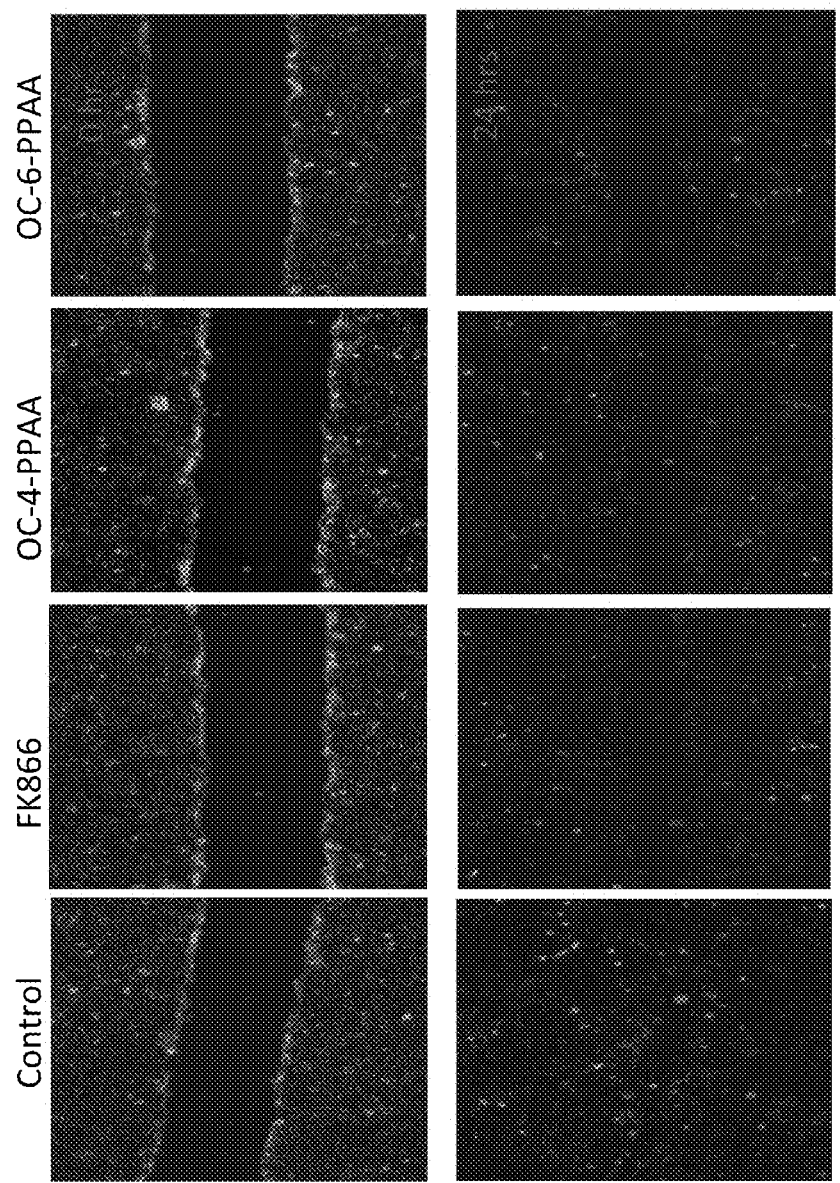
FIG. 13 shows the results of scratch test assays against DLD1 at 0 h and at 24 h.
Figure 14:
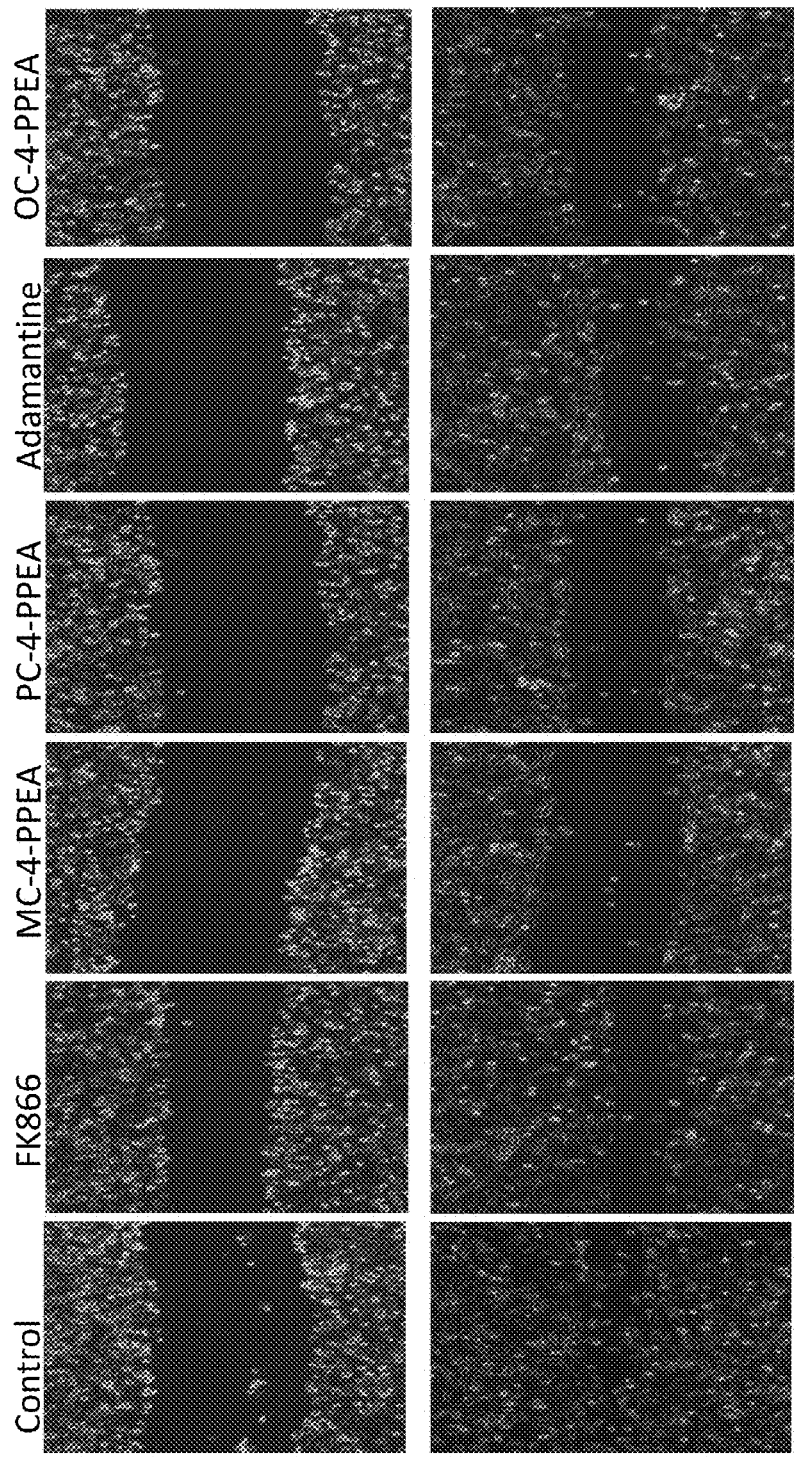
FIG. 14 shows the results of scratch test assays against PC3 at 0 h and at 24 h.

The antimigratory effects of compounds (5)-(7) were compared with FK866 by employing a wound healing or scratch test analysis using various cell cancer lines. The assay measures the ability of a drug to inhibit cancer cell migration across a gap "scratched" in a confluent layer of cells. The cells were imaged immediately after the formation of the wound and then incubated with 1 nM concentrations of each test agent. After 24 h, the wounds were imaged again and compared with a control group of untreated cells. The results are shown in FIG. 9. The control cells repopulated the wound area, whereas treatment with FK866 partially inhibited cell migration. Compounds (5)-(7) inhibited cell migration to a greater extent than FK866, with compound (6) exhibiting the highest potency. The results of the wound healing experiments are consistent with those from the cell viability assays with regard to the relative potencies of the compounds (6)>(7)>(5)>FK866. Additional results are shown in FIGS. 10, 13, and 14.

While the invention has been described in connection with specific embodiments thereof, it will be understood that the inventive device is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth

What is claimed is:

1. A compound comprising Formula (I):

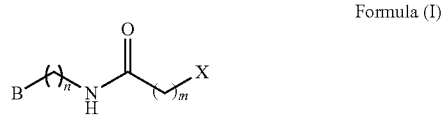

Formula (I)

wherein,

B is a cluster boron;

X is an aromatic moiety having one or more nitrogen atoms;

n is an integer ranging from 1 and 6, and where n is greater than 1, the resulting hydrocarbyl chain may be saturated or unsaturated; and m is an integer ranging from 0 and 4, and where m is greater than 1, the resulting hydrocarbyl chain may be saturated or unsaturated.

2. The compound of claim 1, wherein the cluster boron is a carborane.

3. The compound of claim 1, wherein the cluster boron is a borohydride.

4. The compound of claim 1, wherein n is an integer ranging from 4 and 6 and the resulting hydrocarbyl chain is saturated.

5. The compound of claim 1, wherein m is an integer ranging from 0 and 2.

6. The compound of claim 1, wherein X is 3-pyridyl.

7. The compound of claim 1, wherein the compound comprising Formula (I) is chosen from Formula (5), Formula (6), Formula (7), Formula (33), Formula (34), Formula (35), Formula (36) and Formula (37).

8. The compound of claim 1, wherein the compound comprises Formula (I)(a):

Formula (I)(a)

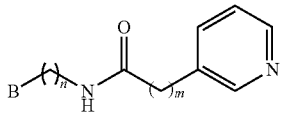

wherein,
B is a cluster boron;
n is an integer ranging from 1 and 6, and where n is greater than 1, the resulting hydrocarbyl chain may be saturated or unsaturated; and
m is an integer ranging from 0 and 4, and where m is greater than 1, the resulting hydrocarbyl chain may be saturated or unsaturated.

9. The compound of claim 1, wherein the compound comprises Formula (I)(b):

Formula (I)(b)

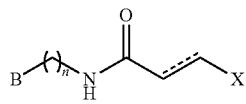

wherein,
B is a cluster boron;
n is an integer ranging from 1 and 6, and where n is greater than 1, the resulting hydrocarbyl chain may be saturated or unsaturated;
the dashed line represents a single or double bond; and
X is an aromatic moiety having one or more nitrogen atoms.

10. The compound of claim 1, in combination with a pharmaceutically acceptable excipient.

11. A method of producing a compound comprising Formula (I):

Formula (I)

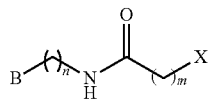

wherein,
B is a cluster boron;
X is an aromatic moiety having one or more nitrogen atoms;
n is an integer ranging from 1 and 6, and where n is greater than 1, the resulting hydrocarbyl chain may be saturated or unsaturated; and
m is an integer ranging between 0 and 4, and where m is greater than 1, the resulting hydrocarbyl chain may be saturated or unsaturated;
the method comprising,
(a). contacting a deprotonated cluster boron with an alkyl dihalide, to produce an alkyl halide substituted cluster boron compound;
(b). contacting the alkyl halide substituted cluster boron with a nitrogen containing compound to produce a compound comprising Formula (II):

Formula (II)

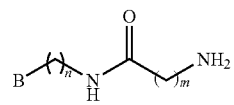

wherein,
B is a cluster boron;
n is an integer ranging from 1 and 6, and where n is greater than 1, the resulting hydrocarbyl chain may be saturated or unsaturated;
m is an integer ranging from 0 and 4, and where m is greater than 1, the resulting hydrocarbyl chain may be saturated or unsaturated; and
(c). contacting the compound comprising Formula (II) with a compound comprising Formula (III):

Formula (III)

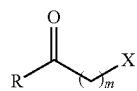

wherein,
R is chosen from OH and Cl;
X is an aromatic moiety having one or more nitrogen atoms; and
m is an integer ranging from 0 and 4, and where m is greater than 1, the resulting hydrocarbyl chain may be saturated or unsaturated,
in the presence of a coupling agent or a base to form the compound comprising Formula (I).

12. The method of claim 11, wherein the cluster boron of step (a) is a silyl protected carborane.

13. The method of claim 11, wherein the alkyl dihalide is chosen from 1-bromo-2-chloroethane, 1-bromo-3-chloropropane, 1-bromo-4-chlorobutane, 1-bromo-5-chloropentane, and 1-bromo-6-chlorohexane.

14. A method of inhibiting NAMPT in a subject, the method comprising administering a subject a compound comprising Formula (I), Formula (I)

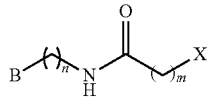

wherein,
B is a cluster boron;
X is an aromatic moiety having one or more nitrogen atoms;
n is an integer ranging from 1 and 6, and where n is greater than 1, the resulting hydrocarbyl chain may be saturated or unsaturated; and
m is an integer ranging from 0 and 4, and where m is greater than 1, the resulting hydrocarbyl chain may be saturated or unsaturated.

15. The method of claim 14, wherein the compound comprising Formula (I) is administered with a pharmaceutically acceptable excipient.

16. The method of claim 14, wherein the cluster boron is a carborane.

17. The method of claim 14, wherein the cluster boron is a borohydride.

18. The method of claim 14, wherein n is an integer ranging from 4 and 6 and the resulting hydrocarbyl chain is saturated.

19. The method of claim 14, wherein the NAMPT inhibition is 10× greater than that by FK866.

20. The method of claim 14, wherein the NAMPT inhibition is 100× greater than that by FK866.

21. The method of claim 14, wherein the antiproliferative effect of the compound comprising Formula (I) is 10× greater than FK866.

22. The method of claim 14, wherein the compound comprising Formula (I) is chosen from Formula (5), Formula (6), Formula (7), Formula (33), Formula (34), Formula (35), Formula (36) and Formula (37).

* * * * *